(12) United States Patent
Inoue et al.

(10) Patent No.: US 6,437,194 B2
(45) Date of Patent: Aug. 20, 2002

(54) PROCESS FOR PREPARING AN ALKYLCYCLOHEXANOL ALKYLENE OXIDE ADDUCT

(75) Inventors: Yoshihisa Inoue; Hiroyoshi Watanabe; Yasuko Ono; Masumi Okita, all of Osaka-fu; Daisuke Fukuoka, Yamaguchi-ken; Yoshio Motoyama, Hiroshima-ken; Kenji Shimamoto, Yamaguchi-ken, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/270,017

(22) Filed: Mar. 16, 1999

(30) Foreign Application Priority Data

| Mar. 23, 1998 | (JP) | 10-073940 |
| Apr. 8, 1998 | (JP) | 10-095734 |
| Sep. 1, 1998 | (JP) | 10-247453 |
| Sep. 1, 1998 | (JP) | 10-247454 |
| Oct. 15, 1998 | (JP) | 10-293149 |

(51) Int. Cl.$^7$ .............................. C07C 41/09
(52) U.S. Cl. ............................ 568/606; 568/670
(58) Field of Search ............................ 568/606, 670

(56) References Cited

U.S. PATENT DOCUMENTS 6,111,146 A * 8/2000 Rayborn ............... 568/606

FOREIGN PATENT DOCUMENTS

| DE | 44-17947 A1 * | 11/1995 |
| FR | 2 354 989 | 1/1978 |
| WO | WO 9911594 | 3/1999 |

OTHER PUBLICATIONS

Translated copy of French Patent 2,354,989, Jan. 1978.*
G.E. Tiller, "Hydrogenation of Triton X–100 Eliminates its Fluorescence and Ultraviolet Light Absorption While Preserving its Detergent Properties", Analytical Biochemistry, vol. 141, 1984, pp. 262–266, XP002105806, p. 262–263.

* cited by examiner

*Primary Examiner*—Rosalynd Keys
(74) *Attorney, Agent, or Firm*—Burns, Doane, Swecker & Mathis, L.L.P.

(57) ABSTRACT

The invention is a preparation process of alkylcyclohexanol alkylene oxide adduct which contains almost no alkylphenol alkylene oxide adduct 1) in the absence of a solvent, 2) in the presence of a saturated hydrocarbon solvent, or 3) in the presence of water.

The invention can prepare alkylcyclohexanol alkylene oxide having a 200 ppm or less content of alkylphenol and alkylphenol alkylene oxide adduct. The alkylcyclohexanol alkylene oxide adduct obtained in the process of the invention has less ultraviolet absorption and fluorescence due to alkylphenol alkylene oxide adduct and is thus useful for spectrometric analysis of protein and further has excellent properties in the field of detergent and other common uses of surface active agents.

1 Claim, No Drawings

US 6,437,194 B2

PROCESS FOR PREPARING AN ALKYLCYCLOHEXANOL ALKYLENE OXIDE ADDUCT

BACKGROUND OF THE INVENTION

1. Field of the Invention

The present invention relates to an alkylcyclohexanol alkylene oxide adduct, and a preparation process and uses of the same. More particularly, the invention relates to an alkylcyclohexanol alkylene oxide adduct which contains a trace amount or less of alkylphenol and alkylphenol alkylene oxide adduct, and a preparation process and uses of the same.

The alkylcyclohexanol alkylene oxide adduct of the invention is useful in the field of surfactants.

2. Description of the Related Art

Higher primary alcohol ethylene oxide adducts and nonylphenol alkylene oxide adduct have been conventionally known as nonionic surfactants. However, higher primary alcohol ethylene oxide adducts have a higher pour point, change to solid when the added molar numbers of ethylene oxide is increased, and become difficult to handle.

Alkylcyclohexanol alkylene oxide adducts also have excellent properties as a nonionic surfactant. Ethylene oxide adducts in particular have a lower pour point, can maintain a liquid state even in a relatively high addition mole number of ethylene oxide, can be handled with ease and thus have received attention as an excellent surfactant.

These alkylcyclohexanol alkylene oxide adducts are specifically useful for protein extraction from cell membrane in the biochemical field. When analyzing the extracted protein by ultraviolet or fluorescent spectrum, conventional alkylcyclohexanol alkylene oxide adduct contains a substantial amount of residual alkylphenol and alkylphenol alkylene oxide adduct and thus the ultraviolet or fluorescent spectrum of these compounds overlaps the spectrum of the extracted protein. As a result, it has a problem of impairing analysis accuracy, and the development of alkylcyclohexanol alkylene oxide adduct containing a less amount of residual alkylphenol and alkylphenol alkylene oxide adduct has been strongly desired.

As to the process for preparing alkylcyclohexanol ethylene oxide adducts and other alkylcyclohexanol alkylene oxide adducts having a higher alkyl group on a side chain of a cyclohexane ring, several processes have been known as shown below.

For example, German Laid-Open Patent 4417947 has disclosed a process for obtaining alkylcyclohexanol by hydrogenation of alkylphenol and successively reacting with ethylene oxide in the presence of a basic catalyst to prepare alkylcyclohexanol ethylene oxide adducts. However, the process leads to a relatively broad addition distribution of ethylene oxide, increases proportion of high molar adduct, and thus results in a solid reaction product which is unfavorable because of difficulty in handling as a surfactant. Further, the reaction of alkylcyclohexanol and other secondary alcohols with ethylene oxide in the presence of a basic catalyst has been generally known to have a very low reaction rate. For example, it has been described in H. Horiguchi ("New Surfactants", page 626, published by Sankyo Shuppan Co. (1975) that ethylene oxide generally reacts very quickly with primary alcohol whereas slowly with secondary alcohol in the presence of a basic catalyst. Consequently, in the preparation of an alkylcyclohexanol ethylene oxide adduct by reaction of alkylcyclohexanol with ethylene oxide in the presence of a basic catalyst, a small amount of alkylcyclohexanol ethylene oxide adduct (primary alcohol) formed in the initial stage of the reaction preferentially reacts with ethylene oxide. As a result, unreacted alkylcyclohexanol remains in an extremely large quantity.

H. Stache et al. have obtained one molar ethylene oxide adduct of isooctylcyclohexanol by hydrogenation of one molar ethylene oxide adduct of isooctylphenol and have successively reacted the product with ethylene oxide to obtain isooctylcyclohexanol ethylene oxide adduct (Tr.-Mezhdunar. Kongr. Poverkhn.-Akt Veshchestvam 7th, Vol. 1(1977), 378-391). However, as to the hydrogenation reaction of one molar ethylene oxide adduct of isooctylphenol, no description can be found at all on the species of the catalyst used and the reaction conditions carried out. Further, no specific purification has been carried out after the hydrogenation reaction. Quite no description has been found on the amount of isooctylphenol ethylene oxide adduct remaining in the isooctylcyclohexanol ethylene oxide adduct thus obtained.

Further, German Patent No. 626965 has also obtained alkylcyclohexanol alkylene oxide adduct by the same process as that of H. Stache et al. The process also did not carry out specific purification of hydrogenation product. No description is found at all on the amount of alkylphenol alkylene oxide adduct remaining in the resulting alkylcyclohexanol alkylene oxide adduct.

Further, George E. Tillar et al. have obtained octylcyclohexanol ethylene oxide adduct by hydrogenation of octylphenol ethylene oxide adduct (Trade Mark: Triton X-100) in an ethanol solvent in the presence of a rhodium carbon catalyst (Analytical Biochemistry 141, 262-266 (1984)). The cited example has suggested that such a process remains 600 ppm of octylphenol ethylene oxide adduct even though the reaction time of hydrogenation is extended.

As mentioned above, several suggestions have been found on the preparation process of alkylcyclohexanol alkylene oxide adducts. However, in the present state of the art, almost no information has been obtained on the preparation process of alkylcyclohexanol alkylene oxide adducts which contain a reduced amount of residual alkylphenol and alkylphenol alkylene oxide adduct, have higher purity and narrow addition distribution of alkylene oxide.

Therefore, the object of the invention is to provide a high purity alkylcyclohexanol alkylene oxide adduct which has a narrow addition distribution of alkylene oxide and contains a trace amount or less of alkylphenol and alkylphenol alkylene oxide adduct, a simple and efficient preparation process of alkylcyclohexanol alkylene oxide adduct, and uses of the same.

SUMMARY OF THE INVENTION

As a result of an intensive investigation in order to solve the above subjects, the present inventors have found a process for efficiently preparing an alkylcyclohexanol alkylene oxide adduct which has a narrow addition distribution of alkylene oxide, contains a trace amount or less of impurities including alkylphenol and alkylphenol alkylene oxide adduct, and is represented by the formula (1). Thus the present invention has been completed.

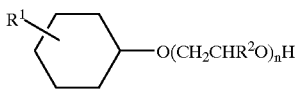

(1)

That is, the first aspect of the invention is an alkylcyclohexanol alkylene oxide adduct which contains 200 ppm or less of alkylphenol and alkylphenol alkylene oxide adduct and is represented by the formula (1):

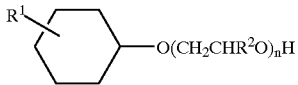

(1)

wherein $R^1$ is an alkyl group having 6 to 20 carbon atoms, $R^2$ is a hydrogen atom, methyl or ethyl group, and n is an integer of 1 or more.

The second aspect of the invention is a preparation process of an alkylcyclohexanol alkylene oxide adduct which contains a trace amount or less of alkylphenol alkylene oxide adduct and is represented by the formula (1), comprising hydrogenating alkylphenol alkylene oxide adduct represented by the formula (2):

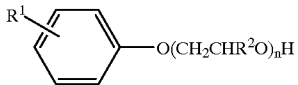

(2)

wherein $R^1$ is an alkyl group having 6 to 20 carbon atoms, $R^2$ is a hydrogen atom, methyl or ethyl group, and n is an integer of 1 or more, 1) in the absence of a solvent, 2) in the presence of a saturated hydrocarbon solvent, or 3) in the presence of water.

The third aspect of the invention is a preparation process of a high purity alkylcyclohexanol alkylene oxide adduct which has a narrow addition distribution of alkylene oxide and is represented by the formula (1), comprising adding one mole of alkylene oxide having 2 to 4 carbon atoms to alkylphenol represented by the formula (4):

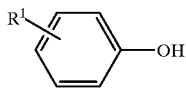

(4)

wherein $R^1$ is an alkyl group having 6 to 20 carbon atoms, thereafter hydrogenating and distillating to obtain alkylene oxide one molar adduct of alkylcyclohexanol which contains a trace amount of alkylphenol and alkylphenol alkylene oxide adduct, and successively adding alkylene oxide in the presence of a basic catalyst.

The fourth aspect of the invention is a preparation process of a high purity alkylcyclohexanol alkylene oxide adduct which has a narrow addition distribution of alkylene oxide and is represented by the formula (1), comprising hydrogenating alkylphenol represented by the formula (4), thereafter distillating to obtain alkylcyclohexanol which contains a trace amount of alkylphenol, and successively adding alkylene oxide having 2 to 4 carbon atoms in the presence of an acid catalyst, and further distillating the reaction product.

DETAILED DESCRIPTION OF THE PREFERRED EMBODIMENTS

Alkylcyclohexanol alkylene oxide adduct of the present invention is represented by the formula (1):

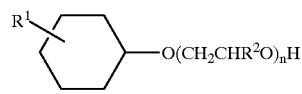

(1)

wherein $R^1$ is an alkyl group having 6 to 20 carbon atoms, $R^2$ is a hydrogen atom, methyl or ethyl group, and n is an integer of 1 or more, and corresponds to the nuclear hydrogenation product of alkylphenol alkylene oxide adduct represented by the formula (2):

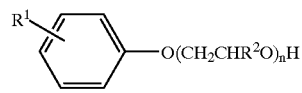

(2)

wherein $R^1$ is an alkyl group having 6 to 20 carbon atoms, $R^2$ is a hydrogen atom, methyl or ethyl group, and n is an integer of 1 or more.

On the formula (2) of alkylphenol alkylene oxide adduct in the invention, $R^1$ is an alkyl group having 6 to 20 carbon atoms. No particular restriction is imposed upon the structure of $R^1$. $R^1$ can be a straight chain structure or branched structure or any isomeric structure of an alkyl group. The attached position of $R^1$ can be any of the 2, 3 or 4 position to the alkoxylate group ($-O(CH_2CHR^2O)_n$ H group) on the benzene ring. Further, $R^2$ in the oxyalkylene units ($-CH_2CHR^2O-$ units) is a hydrogen atom, methyl or ethyl group. Oxyalkylene units are specifically oxyethylene units ($-CH_2CH_2O-$units), oxypropylene units ($-CH_2CH(CH_3)O-$ units) or oxybutylene units ($-CH_2CH(CH_2CH_3)O-$ units). n is an integer of 1 or more. When n is 2 or more, recurring units can have only one of the oxyethylene units, oxypropylene units or oxybutylene units, or can have 2 or more oxyalkylene units. When 2 or more species of oxyalkylene units are present, the units can be in a random addition or block addition. No particular limitation is imposed upon the range of n. However, n is usually in the range of 1 to 50. When n is 1, the compound can be specifically one molar adduct of alkylene oxide or one molar alkylene oxide adduct.

Alkylphenol alkylene oxide adduct represented by the formula (2) includes structural isomers of $R^1$ and an alkoxylate group, and compounds which differ in the species and numbers and numbers of the oxyalkylene group. These compounds can be used singly and are usually used as a mixture. Further, these compounds can be a mixture of two species or more alkylphenol alkylene oxide adducts which are represented by the formula (2) and differ in the carbon numbers of the alkyl group $R^1$.

Specific alkylphenol alkylene oxide adducts represented by the formula (2) include, for example, ethylene oxide adduct of hexylphenol, heptylphenol, octylphenol, nonylphenol, decylphenol, undecylphenol, tridecylphenol, tetradecylphenol, pentadecylphenol, hexadecylphenol, heptadecylphenol, octadecylphenol, nonadecylphenol, eicosylphenol and other alkylphenols; for example, propylene oxide adduct of hexylphenol, heptylphenol, octphenol, nonylphenol, decylphenol, undecylphenol, tridecylphenol, tetradecylphenol, pentadecylphenol, hexadecylphenol, heptadecylphenol, octadecylphenol, nonadecylphenol eicosylphenol and other alkylphenols; for example, butyleneoxide adduct of hexylphenol, heptylphenol, octylphenol, nonylphenol, decylphenol, undecylphenol, tridecylphenol, tetradecylphenol, pentadecylphenol, hexadecylphenol, heptadecylphenol, octadecylphenol, nonadecylphenol, eicosylphenol and other alkylphenols; for example, octylphenol (ethylene oxide/propylene oxide) random copolymer, octylphenol(ethylene oxide/butylene oxide) random copolymer, octylphenol(propylene oxide/butylene oxide) random copolymer, nonylphenol(ethylene oxide/propylene oxide) random copolymer nonylphenol(ethylene oxide/butylene oxide) random copolymer, nonylphenol(propylene oxide/butylene oxide) random copolymer and other alkylphenol alkylene oxide random copolymers; and for example, octylphenol(ethylene oxide/propylene oxide) block copolymer, octylphenol(ethylene oxide/butylene oxide) block copolymer, octylphenol(propylene oxide/butylene oxide) block copolymer, nonylphenol(ethylene oxide/propylene oxide) block copolymer, nonylphenol (ethylene oxide/butylene oxide) block copolymer, nonylphenol(propylene oxide/butylene oxide) block copolymer and other alkylphenol alkylene oxide block copolymers.

Further, alkylcyclohexanol of the invention is represented by the formula (3):

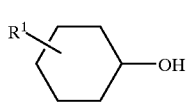

(3)

wherein $R^1$ is an alkyl group having 6 to 20 carbon atoms, and corresponds to the hydrogenation product of alkylphenol represented by the formula (4):

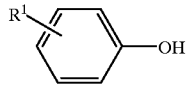

(4)

wherein $R^1$ is an alkyl group having 6 to 20 carbon atoms.

On the formula (4) of alkylphenol in the invention, $R^1$ is an alkyl group having 6 to 20 carbon atoms. No particular restriction is imposed upon the structure of $R^1$. $R^1$ can be a straight chain structure or branched structure or any isomeric structure of an alkyl group. The attached position of $R^1$ can be any of the 2, 3 or 4 position to the hydroxyl group (—OH group) on the benzene ring. Alkylphenol represented by the formula (4) has structural isomers of $R^1$ and hydroxyl group. These isomers can be usually used as a mixture and can also be used singly. Further, a mixture of alkylphenols which differ in the number of carbon atom on the alkyl group $R^1$ can also be used.

Representative alkylphenols represented by the formula (4) include, for example, hexylphenol, heptylphenol, octylphenol nonylphenol, decylphenol, undecylphenol, tridecylphenol, tetradecylphenol, pentadecylphenol, hexadecylphenol, heptadecypylphenol octadecylphenol, nonadecylphenol, eicosylphenol, and other alkylphenols.

Further, alkylene oxides having 2 to 4 carbon atoms in the invention specifically include ethylene oxide, propylene oxide and butylene oxide. These alkylene oxides can be used singly or as a mixture. When two or more alkylene oxides are used as a mixture both random addition and block addition can be carried out.

The alkylcyclohexanol alkylene oxide adduct which has a narrow addition distribution of alkylene oxide, and contains a trace amount or less of alkylphenol and alkylphenol alkylene oxide adduct can be prepared by the preparation processes (A) to (E) below.

Preparation Process (A)

The alkylcyclohexanol alkylene oxide adduct of the invention represented by the formula (1);

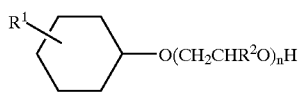

(1)

wherein $R^1$ is an alkyl group having 6 to 20 carbon atoms, $R^2$ is a hydrogen atom, methyl or ethyl group, and n is an integer of 1 or more, is prepared by reacting alkylphenol alkylene oxide adduct represented by the formula (2):

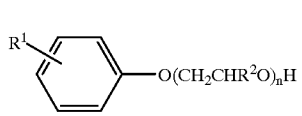

(2)

wherein $R^1$, $R^2$ and n are the same as above, with hydrogen under hydrogen gauge pressure exceeding 2.0 MPa, at temperature of 80 to 150° C., in the absence of a solvent, and in the presence of a supported catalyst of ruthenium or rhodium.

The process is characterized by reacting alkylphenol alkylene oxide adduct with hydrogen in the absence of a solvent. The reaction in the absence of a solvent can provide the desired alkylcyclohexanol alkylene oxide adduct in a high degree of conversion merely by removing the catalyst without solvent recovery procedure.

The process reacts alkylphenol alkylene oxide adduct with hydrogen in the presence of a supported catalyst of ruthenium or rhodium. Representative supported catalysts of ruthenium or rhodium include, for example, ruthenium carbon, rhodium carbon and other carbon supported catalysts of these metals; ruthenium alumina, rhodium alumina and other alumina supported catalysts of these metals; and ruthenium titania and other titania supported catalyst of these metals. No particular limitation is imposed upon the supported amount of these metals. The amount is usually in the range of 0.01 to 20% by weight. These catalysts can be crushed or powdered or molded into pellet or sphere. In these catalysts, ruthenium or rhodium catalyst supported on carbon or alumina is preferred in view of excellent activity and selectivity.

In the process, the reaction is carried out at temperature of 80 to 150° C. under hydrogen gauge pressure exceeding 2.0 MPa in order to prepare alkylcyclohexanol alkylene oxide adduct in good efficiency and high selectivity. When the hydrogen gauge pressure is 2.0 MPa or less, the hydrogenation reaction is very slow. On the other hand, the gauge pressure exceeding 15 Mpa requires very high pressure resistance to the reactor and thus the upper limit of the hydrogen pressure is preferably gauge pressure of 15 Mpa. Further, the reaction temperature less than 80° C. leads to very low reaction rate of hydrogenation reaction. On the other hand, the reaction temperature exceeding 150° C. tends to cause side reactions such as cleavage of ether bonds due to a hydrogenation decomposition reaction, and unfavorably lowers selectivity of alkylcyclohexanol alkylene oxide adduct. More preferred hydrogen pressure and reaction temperature differ depending upon species and amount of the catalyst used and numbers of oxyalkylene units in the alkylcyclohexanol alkylene oxide adduct and are suitably selected in the specified ranges of hydrogen pressure and reaction temperature.

No particular restriction is imposed upon the procedures for carrying out the reaction. Batch procedure, semi-batch procedure and continuous procedure can be carried out. No particular limitation is put upon the amount of the catalyst in the batch and semi-batch procedures. The amount of the catalyst is usually in the range of 0.5 to 50% by weight for the alkylphenol alkylene oxide adduct used as a raw material. The reaction time is usually in the range of 0.5 to 50 hours. When the reaction is carried out by the continuous procedure, reaction conditions differ depending upon the species of the catalyst and other factors. LHSV is usually in the range of 0.01 to 50 hr$^{-1}$.

Preparation Process (B)

Alkylcyclohexanol alkylene oxide adduct of the invention represented by the formula (1):

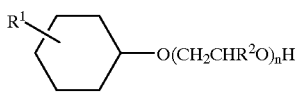

(1)

wherein $R^1$ is an alkyl group having 6 to 20 carbon atoms, $R^2$ is a hydrogen atom, methyl or ethyl group, and n is an integer of 1 or more, can also be prepared by reacting alkylphenol alkylene oxide adduct represented by the formula (2):

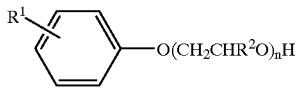

(2)

wherein $R^1$, $R^2$ and n are the same as above, with hydrogen in the presence of water by use of a supported catalyst of ruthenium, rhodium, palladium or platinum.

Alkylcyclohexanol alkylene oxide adduct of the invention is characterized by reacting alkylphenol alkylene oxide adduct with hydrogen in the presence of water by use of a supported catalyst of ruthenium, rhodium, palladium or platinum.

The catalyst used for the process can be a supported catalyst of ruthenium, rhodium, palladium or platinum. Representative supported catalysts of ruthenium, rhodium, palladium and platinum include, for example, ruthenium carbon, rhodium carbon, palladium carbon, platinum carbon and other carbon supported catalysts of these metals; ruthenium alumina, rhodium alumina and other alumina supported catalysts of these metals; palladium silica alumina, platinum silica alumina and other silica alumina supported catalysts of these metals; palladium silica magnesia, and other silica magnesia supported catalysts of these metals; palladium zeolite and other zeolite supported catalysts of these metals; palladium barium sulfate and other barium sulfate supported catalysts of these metals; and ruthenium titania and other titania supported catalysts of these metals. Further, catalysts supported by two species or more metals at the same time in an arbitrary proportion can also be used.

Exemplary catalysts of such type include, for example, ruthenium-rhodium carbon, palladium-platinum carbon and other carbon supported catalysts of these metals; and ruthenium-rhodium alumina, palladium-platinum alumina and other alumina supported catalysts of these metals. These supported catalysts can be used singly or as a mixture of any proportion. No particular limitation is put upon the supported amount of these metals. The supported amount is usually in the range of 0.01 to 20% by weight. These catalysts can be powdered, crushed or molded into pellet or globe. Further, water containing catalyst which can be commonly obtained with ease in the market can preferably be used.

In these supported catalysts, carbon or alumina supported catalyst of ruthenium is preferably used in view of excellent activity and selectivity.

The process carries out reaction in the presence of water. The water charged to the reaction system can be previously dissolved, dispersed or impregnated into the raw material such as alkylphenol alkylene oxide adduct, catalyst or solvent, when used, or can also be independently charged to the reaction system.

No particular limitation is imposed upon the amount of water. The amount of water is usually in the range of 1 to 50% by weight, preferably 1 to 40% by weight for the amount of alkylphenol alkylene oxide adduct used for the raw material.

The process can be carried out in the presence or absence of a solvent. Any type of a solvent can be used so long as the solvent, when used, can dissolve or disperse the raw material alkylphenol alkylene oxide adduct and the solvent itself cannot be hydrogenated.

Exemplary solvents which can be used include, for example, methanol, ethanol, isopropyl alcohol, t-butylalcohol, cyclohexanol, 4-methylcyclohexanol, 1,2-ethanediol, glycerol and ether alcohol compounds; pentane, hexane, heptane, 2-methylpentane and other aliphatic hydrocarbon compounds; cyclopentane, cyclohexane, methylcyclohexane, ethylcyclohexane, bicyclohexyl, decalin and other aliphatic cyclic hydrocarbon compounds; dichloromethane, carbon tetrachloride, butyl chloride, propyl bromide, chlorocyclohexanol and other halogenated hydrocarbon compounds; diethyl ether, diisopropyl ether, dioxane, tetrahydrofuran 1,2-dimethoxyethane and other ether compounds; acetone, methyl ethyl ketone, diisobutyl ketone, acetylacetone and other ketone compounds; methyl formate, ethyl acetate, ethylene carbonate and other ester compounds; and nitromethane, acetonitrile and other nitrogen compounds. These solvents can be used singly or as a mixture.

Specifically, when alcohol compounds such as ethanol are used as a solvent, the hydrogenating reaction in the absence of water has a very low rate of reaction and leaves a large amount of unreacted alkylphenol alkylene oxide adduct. However, it is surprising that, when the hydrogenation reaction is carried out in alcohol compounds in the presence of water, the reaction rate is extremely accelerated and almost no unreacted alkylphenol alkylene oxide adduct remains after the hydrogenation reaction.

The reaction is usually carried out at reaction temperature of 30 to 200° C., preferably 50 to 150° C. under the hydrogen gauge pressure of 0 to 20 MPa, preferably 0.5 to 15 MPa. More preferred hydrogen pressure and reaction temperature differ depending upon the species and amount of the catalyst used and the numbers of oxyalkylene units in the alkylphenol alkylene oxide adduct, and are suitably selected.

No particular restriction is put upon the procedures for carrying out the reaction. Batch procedure, semi-batch procedure and continuous procedure can be carried out. No particular limitation is imposed upon the amount of the catalyst in the batch and semi-batch procedures. The amount of the catalyst is usually in the range of 0.5 to 50% by weight for the alkylphenol alkylene oxide adduct used as a raw material. The reaction time is usually in the range of 0.5 to 50 hours. When the reaction is carried out by the continuous procedure, reaction conditions differ depending upon the species of the catalyst and other factors. LHSV is usually in the range of 0.01 to 50 $hr^{-1}$.

Preparation Process (C)

Alkylcyclohexanol alkylene oxide adduct of the invention represented by the formula (1):

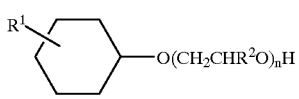

(1)

wherein $R^1$ is an alkyl group having 6 to 20 carbon atoms, $R^2$ is a hydrogen atom, methyl or ethyl group, and n is an integer of 1 or more, can also be prepared by reacting alkylphenol alkylene oxide adduct represented by the formula (2):

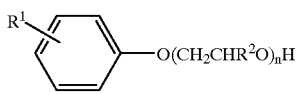

(2)

wherein $R^1$, $R^2$ and n are the same as above, with hydrogen in the saturated hydrocarbon solvent in the presence of a hydrogenation catalyst.

The hydrogenation catalyst used in the process can be the same supported catalyst of ruthenium, rhodium, palladium or platinum which can be used in the preparation process (B), as mentioned above. These supported catalysts can be used singly or as a mixture of any proportion. No particular limitation is put upon the supported amount of these metals. The supported amount is usually in the range of 0.01 to 20% by weight. These catalysts can be powdered, crushed or molded into pellet or globe. Further, water containing catalyst which can be commonly obtained with ease in the market can preferably be used.

In these catalysts, the ruthenium catalyst supported on carbon or alumina is preferred in view of excellent catalytic activity and selectivity.

The process is characterized by carrying out in the presence of a saturated hydrocarbon solvent. No particular restriction is imposed upon the structure of the saturated hydrocarbon solvent used. The solvents having straight chain structure, branched structure and cyclic structure can be used. Any type of solvent can be used so long as the solvent can dissolve or disperse the raw material alkylphenol alkylene oxide adduct of the formula (2) and the product alkylcyclohexanol alkylene oxide adduct of the formula (1) and the solvent itself cannot be hydrogenated. Representative solvents which can be used in the process include, for example, n-pentane, n-hexane, n-heptane, n-octane, n-dodecane and other straight chain saturated hydrocarbons; 2-methylbutane, 2-methylpentane, 2-methylhexane, 2-methylheptane, 3-methylpentane, 3- ethylpentane, 3-methylhexane, 3-ethylhexane, 3-methylheptane, 2,2-dimethylpropane, 2,2-dimethylbutane, 2,2-dimethylhexane, 2,3-dimethylbutane, 3-methyl-3-ethylpentane, 2,2,3-trimethylbutane and other branched saturated hydrocarbons; and cyclopentane, cyclohexane, decalin, methylcyclopentane, methylcyclohexane, p-menthane and other cyclic saturated hydrocarbons. These solvents can be used singly or as a mixture. In these saturated hydrocarbon solvents, cyclic saturated hydrocarbon is particularly preferred in view of reactivity and selectivity. No particular limitation is imposed upon the amount of the saturated hydrocarbon solvent. The amount of the solvent used is commonly in the range of providing a concentration of 5 to 80% by weight, preferably 20 to 60% by weight for the raw material alkylphenol alkylene oxide adduct.

In proceeding the reaction, the presence of water is preferred because reaction rate is enhanced without giving an adverse effect on the selectivity of the reaction. Water, when used, can be previously dissolved, dispersed or impregnated in the raw material alkylphenol alkylene oxide adduct of the formula (2), catalyst or solvent, or can be independently charged to the reaction system. No particular limitation is imposed on the amount of water. The amount of water is usually in the range of 0.1 to 50% by weight, preferably 1 to 40% by weight for the raw material alkylphenol alkylene oxide adduct of the formula (2).

Hydrogen pressure and reaction temperature of the process are the same as those used in the preparation process (B). More preferred hydrogen pressure and reaction temperature differ depending upon the species and amount of the catalyst used and numbers of oxyethylene units in the alkylphenol alkylene oxide adduct of the formula (2), and thus these reaction conditions are arbitrarily selected.

No particular restriction is imposed upon the procedure of the reaction. Batch procedure, semi-batch procedure and continuous procedure can be carried out. When the reaction is carried out by batch or semi-batch procedures, no particular limitation is imposed upon the amount of catalyst. The amount is usually in the range of 0.5 to 50% by weight for the raw material alkylphenol alkylene oxide adduct of the formula (2). The reaction time is commonly in the range of 0.5 to 50 hours. When the reaction is carried out by continuous procedures, the reaction conditions differ depending upon the species of the catalyst. LHSV is usually in the range of 0.01 to 50 $hr^{-1}$.

Preparation processes (A), (B) and (C) can provide alkylcyclohexanol alkylene oxide adduct containing 200 ppm or less of unreacted alkylphenol alkylene oxide adduct.

Alkylcyclohexanol alkylene oxide adduct having further decreased content of alkylphenol alkylene oxide adduct and alkylphenol can be obtained by below described preparation processes (D) and (E) which have an added step of distillation.

Preparation Process (D)

In the process, the preparation of high purity alkylcyclohexanol alkylene oxide adduct represented by the formula (1);

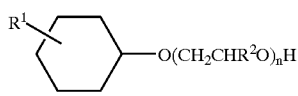

(1)

wherein $R^1$ is an alkyl group having 6 to 20 carbon atoms, $R^2$ is a hydrogen atom, methyl or ethyl group, and n is an integer of 1 or more, is characterized by consisting of below described four steps;
1) the first alkylene oxide addition step for reacting 1 mole of alkylphenol represented formula (4);

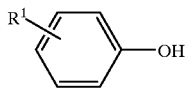

(4)

wherein R¹ is an alkyl group having 6 to 20 carbon atoms, with 0.9 to 1.2 moles of alkylene oxide having 2 to 4 carbon atoms in the presence of a basic catalyst to obtain a formed product primarily consisting of one molar alkylene oxide adduct of alkylphenol,
2) the hydrogenation step for reacting the formed product of the first alkylene oxide addition step with hydrogen in the presence of a hydrogenation catalyst to obtain a formed product primarily consisting of one molar alkylene oxide adduct of alkylcyclohexanol,
3) the distillation step for distillating the formed product of the hydrogenation step to obtain a fraction primarily consisting of one molar alkylene oxide adduct of alkylcyclohexanol and containing 10 ppm by weight or less in the sum of alkylphenol and alkylphenol alkylene oxide adduct, and
4) the second alkylene oxide addition step for reacting the fraction obtained in the distillation step and primarily consisting of one molar alkylene oxide adduct of alkylcyclohexanol with alkylene oxide in the presence of a basic catalyst.

The alkylene oxide having 2 to 4 carbon atoms which can be used in the first and second alkylene oxide addition steps includes, for example, ethylene oxide, propylene oxide and butylene oxide. Alkylene oxide can be used singly or as a mixture. When alkylene oxide is used as a mixture, both random and block addition can be carried out.

Exemplary, basic catalysts which are used in the first alkylene oxide addition step include, for example, sodium hydroxide, potassium hydroxide, cesium hydroxide and other alkali metal hydroxides; sodium ethoxide, lithium ethoxide, potassium phenoxide and other alkali metal alkoxides or phenoxides; calcium hydroxide, barium hydroxide, strontium hydroxide and other alkali earth metal hydroxides; calcium methoxide, calcium phenoxide and other alkali earth metal alkoxides or phenoxides; magnesium oxide, barium oxide and other alkali earth metal oxides. In these basic catalysts, alkali metal hydroxides are preferably used. Amount of the catalyst differs depending upon the species of the catalyst and reaction temperature and reaction temperature and is usually in the range of 10 to 5,000 ppm by weight for the raw material alkylphenol.

The basic catalyst which is soluble in the reaction product can be converted to a soluble salt of organic acid by neutralizing with an organic acid after the reaction, or can be neutralized with a mineral acid such as sulfuric acid and the precipitated mineral acid salt is removed by filtration. Alternatively, the reaction mass can be used as intact to the next hydrogenation step without neutralization. Further, the catalyst which is insoluble in the reaction product can be usually removed by filtration and successively the next hydrogenation step is carried out.

The first alkylene oxide addition step reacts 1 mole of alkylphenol with 0.9 to 1.2 moles of alkylene oxide having 2 to 4 carbon atoms and primarily prepares one molar alkylene oxide adduct of alkylphenol. When addition amount of alkylene oxide is less than the above range, an increased amount of unreacted alkylphenol remains after the reaction. On the other hand, the addition amount of alkylene oxide more than the above range increases formation of compounds having two moles or more alkylene oxide addition to alkylphenol.

The object of the first alkylene oxide addition step is to prepare one molar ethylene oxide adduct of alkylphenol which can maintain primary alcohol even after the hydrogenation step and can be readily purified by distillation. Thus, it is unfavorable to leave a substantial amount of alkylphenol which converts to secondary alcohol after the hydrogenation step, or to form a substantial amount of two or more molar alkylene oxide adduct of alkylphenol which has a high boiling point and is difficult to purify by distillation.

The reaction temperature in the first alkylene oxide addition step is usually in the range of 60 to 230° C., preferably 120 to 200° C. The reaction time is usually in the range of 0.1 to 30 hours, preferably 0.3 to 20 hours. The gauge pressure in the reaction is usually in the range of 0 to 2 MPa, preferably 0.1 to 0.7 MPa. Any of the batch procedure, semi-batch procedure and continuous procedure can be carried out.

The hydrogenation catalysts which are used in the hydrogenation step of the process can be any species of the catalyst so long as the catalysts is capable of hydrogenating the aromatic ring of the formed product which is obtained in the first alkylene oxide addition step and primarily consisting of one molar alkylene oxide adduct of alkylphenol, with hydrogen to obtain a cyclohexane ring. Representative of such catalysts include, for example, supported catalysts of ruthenium, rhodium, palladium and platinum, complex catalysts of these metals, and Raney nickel and Raney cobalt. Specific supported catalysts of ruthenium, rhodium, palladium, and platinum include, for example, ruthenium carbon, rhodium carbon, palladium carbon, platinum carbon and other carbon supported catalysts of metals, ruthenium alumina, rhodium alumina and other alumina supported catalysts of metals; palladium silica alumina and other silica alumina supported catalysts of metals; palladium zeolite and other zeolite supported catalysts of metals; palladium barium sulfate and other barium sulfate supported catalysts of metals; and ruthenium titania and other titania supported catalysts of metals. No particular limitation is imposed upon the supported amount of metals. The amount is usually in the range of 0.01 to 20% by weight. These catalysts can be powdered, crushed or molded into pellet or sphere.

Representative complex catalysts of ruthenium, rhodium, palladium and platinum include, for example, ruthenium chloride, palladium bromide and other halogenides of metal; palladium acetate, rhodium propionate and other carboxylates of metal; palladium acetylacetonate, ruthenium acetylacetonate and other acetylacetonate complexes of metal; and dichlorotris-(triphenylphosphine) ruthenium, chlorotris (triphenylphosphine) rhodium, dichlorobis (triphenylphosphine) palladium, dichlorobis (triphenylphosphine) platinum and other phosphine complex of these metals. These complex catalysts can be used singly or as a mixture.

In these catalysts, carbon or alumina supported catalysts of ruthenium or rhodium and Raney nickel are preferred in view of excellent catalytic activity and selectivity.

In the hydrogenation step of the process, hydrogen pressure is usually in the range of gauge pressure of 0 to 20 MPa, preferably 0.5 to 15 MPa in the gauge pressure. Reaction temperature is usually in the range of 30 to 200° C., preferably 50 to 150° C.

The reaction can be carried out in the presence or absence of a solvent. Any solvent can be used for the process so long as the solvent can dissolve or disperse the raw material, one molar alkylene oxide adduct of alkylphenol and one molar alkylene oxide adduct of corresponding alkylcyclohexanol which is a formed product and the solvent itself does not react with hydrogen in the above reaction conditions. The solvents used in the preparation process (B) can be used as intact for the process.

In these solvents, aliphatic hydrocarbon compounds and aliphatic cyclic hydrocarbon compounds are preferably used, and aliphatic cyclic hydrocarbon compounds are preferred in particular. No particular limitation is imposed upon the amount of solvents. The amount is usually in the range of providing a concentration of usually 5 to 80% by weight, preferably 20 to 60% by weight for the raw material, one molar alkylene oxide adduct of alkylphenol.

When one molar alkylene oxide adduct of alkylphenol is reacted with hydrogen in the presence of a solvent, the reaction rate is sometimes low and preferable yield cannot be obtained in the reaction. Particularly, ethanol and other alcohol solvents require a long reaction time and lead to inferior productivity. In such a case, the reaction can be preferably carried out in the presence of water because the reaction rate is preferably accelerated without giving an adverse effect on the selectivity. Water, when used, can be previously dissolved, dispersed or impregnated into the raw material, one molar alkylene oxide adduct of alkylphenol, catalyst or solvent, or can be independently charged to the reaction system. No particular limitation is imposed upon the amount of water. The amount is usually in the range of 0.1 to 50% by weight, preferably 1 to 40% by weight for the raw material, one molar alkylene oxide adduct of alkylphenol.

No particular restriction is put upon the procedures for carrying out the reaction. Any of batch procedure, semibatch procedure and continuous procedure can be carried out. No particular limitation is imposed upon the amount of catalyst when the reaction is carried out by batch or semibatch procedure. The amount of catalyst is usually in the range of 0.5 to 50% by weight for the raw material one molar alkylene oxide adduct of alkylphenol. The reaction time is usually in the range of 0.5 to 50 hours. When the reaction is carried out by the continuous procedure, reaction conditions differ depending upon the species of the catalyst used and is usually in the range of 0.01 to 50 hr$^{-1}$ in LHSV. After finishing the reaction, the formed product which is primarily consisting of one molar alkylene oxide adduct of alkylcyclohexanol can be obtained by removing the catalyst with a common solid-liquid separation method. When the solvent is used, the formed product desired can be obtained by separating the catalyst from the reaction mass and distilling off the solvent from the filtrate.

In the process, the formed product obtained in the hydrogenation step is distilled to provide a fraction consisting primary of one molar alkylene oxide adduct of alkylcyclohexanol and containing 10 ppm by weight or less in the sum of unreacted alkylphenol and alkylphenol alkylene oxide adduct. The term alkylphenol alkylene oxide adduct refers to any compounds obtained by adding one molar or more alkylene oxide to alkylphenol. The object of the distillation step is to fractionate alkylphenol and alkylphenol alkylene oxide adduct and to obtain a fraction which is almost free from these compounds and primarily consists of one molar alkylene oxide adduct of alkylcyclohexanol. The fraction can contain a small amount of alkylcyclohexanol and two molar or more alkylene oxide adduct of alkylcyclohexanol. The distillation can be carried out by batch or continuous procedures.

In the second alkylene oxide addition step, a fraction of distillation step consisting primarily of one molar alkylene oxide adduct of alkylcyclohexanol is reacted with alkylene oxide having 2 to 4 carbon atoms in the presence of a basic catalyst to obtain high purity alkylene oxide adduct of alkylcyclohexanol.

The basic catalysts used in the step are the same as used in the first alkylene oxide addition step. Alkali metal hydroxide is preferred in these basic catalysts. The amount of the catalyst is usually in the range of 10 to 5,000 ppm by weight for the raw material fraction consisting primarily of one molar alkylene oxide adduct of alkylcyclohexanol. No particular restriction is imposed upon the addition numbers of alkylene oxide. The numbers are suitably selected depending upon uses of the alkylene oxide adduct obtained. Reaction temperature and reaction pressure are usually the same as those in the first alkylene oxide addition step. Reaction time differs depending upon the amount of alkylene oxide to be added and is usually in the range of 0.5 to 50 hours.

The alkylcyclohexanol alkylene oxide adduct obtained in the preparation processes (D) and represented by the formula (1) has a 10 ppm or less content of alkylphenol and alkylphenol alkylene oxide adduct, has a narrow addition distribution, and can be used as a material of surface active agents.

Preparation Process (E)

The process for preparing high purity alkylcyclohexanol alkylene oxide adduct represented by the formula (1); is characterized by consisting of below described four steps;

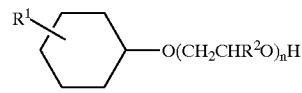

(1)

wherein $R^1$ is an alkyl group having 6 to 20 carbon atoms, $R^2$ is a hydrogen atom, methyl or ethyl group, and n is an integer of 1 or more, 1) the hydrogenation step for reacting alkylphenol represented by the formula (4);

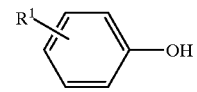

(4)

wherein $R^1$ is an alkyl group having 6 to 20 carbon atoms, with hydrogen in the presence of a hydrogenation catalysts to obtain a formed product primarily consisting of corresponding alkylcyclohexanol represented by the formula (3);

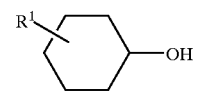

(3)

wherein R1 is the same as above, 2) the first distillation step for distillating the formed product obtained in the hydrogenation step to provide alkylphenol content of 10 ppm by weight or less in the fraction primarily consisting of alkylcyclohexanol, 3) an alkylene oxide addition step for reacting one mole of alkylcyclohexanol obtained in the first distillation step with 1 to 5 moles of alkylene oxide having 2 to 4 carbon atoms in the presence of an acid catalyst to prepare alkylcyclohexanol alkylene oxide adduct, and 4) the second distillation step for separating unreacted alkylcyclohexanol and low boiling-point byproduct of the reaction from alkylcyclohexanol alkylene oxide adduct obtained in the alkylene oxide addition step.

The hydrogenation step of the process can use the same catalyst as used in the preparation process (D).

Hydrogen pressure in the hydrogenation step of the process is usually in the range of gauge pressure 0 to 20 MPa, preferably 0.5 to 15 MPa. Reaction temperature is usually in the range of 30 to 200° C., preferably 50 to 150° C.

The reaction can be carried out in the presence or absence of a solvent. Any solvent can be used for the process so long as the solvent can dissolve or disperse the raw material alkylphenol and corresponding alkylcyclohexanol which is a formed product and the solvent itself does not react with hydrogen in the above reaction conditions. The solvents used in the preparation process (B) can be used as intact for the process.

In these solvents, aliphatic hydrocarbon compounds and aliphatic cyclic hydrocarbon compounds are preferably used, and aliphatic cyclic hydrocarbon compounds are preferred in particular. No particular limitation is imposed upon the amount of solvents. The amount is usually in the range of providing a concentration of usually 5 to 80% by weight, preferably 20 to 60% by weight for the raw material alkylphenol.

When alkylphenol is reacted with hydrogen in the presence of a solvent, the reaction rate is sometimes low and preferable yield cannot be obtained in the reaction. Particularly, ethanol and other alcohol solvents require a long reaction time and lead to inferior productivity. In such a case, the reaction can be preferably carried out in the presence of water because the reaction rate is preferably accelerated without giving an adverse effect on the selectivity. Water, when used, can be previously dissolved, dispersed or impregnated into the raw material alkylphenol of the formula (3), catalyst or solvent, or can be independently charged to the reaction system. No particular limitation is imposed upon the amount of water. The amount is usually in the range of 0.1 to 50% by weight, preferably 1 to 40% by weight for the raw material alkylphenol.

No particular restriction is imposed upon the reaction procedures in the hydrogenation step. Any of batch procedure, semi-batch procedure and continuous procedure can be carried out. When the reaction is carried out by batch or semi-batch procedure, no particular limitation is put upon the amount of the catalyst. The amount is usually in the range of 0.5 to 50% by weight for the raw material alkylphenol. The reaction time is usually in the range of 0.5 to 50 hours. When the reaction is carried out by the continuous procedure, the reaction conditions differ depending upon the species of the catalyst used and LHSV is usually in the range of 0.01 to 50 hr$^{-1}$. After finishing the reaction, the formed product which consists primarily of alkylcyclohexanol can be obtained by separating the catalyst with a usual solid-liquid separation method. When a solvent is used, the desired product can be obtained by distillating off the solvent after separating the catalyst from the reaction mixture.

In a formed product obtained in the hydrogenation step and composed primarily of alkylcyclohexanol, unreacted alkylphenol remains though in a trace amount. The residual alkylphenol influences the successive reaction and leads to quality reduction of the final product alkylcyclohexanol alkylene oxide adduct. Accordingly, the first distillation step below is carried out.

The first distillation step of the invention distillates the formed product in the hydrogenation step and reduces the content of alkylphenol to 10 ppm by weight or less in the fraction consisting of alkylcyclohexanol. The object of the distillation step is to obtain an alkylcyclohexanol fraction containing a trace amount or less of impurity by separating alkylphenol with distillation. Accordingly, a distillation apparatus equipped with a rectifying column and a reflux condenser can be used. The distillation can be carried out at atmospheric pressure or under reduced pressure.

Further, a high purity alkylcyclohexanol fraction containing a trace amount or less of alkylphenol can be obtained by carrying out the distillation step in the presence of a basic compound without using the rectification, column, reflux condenser and other high grade distillation equipment. The basic compounds which can be used in the distillation step are organic and inorganic compounds having basicity and include, for example, sodium hydroxide, potassium hydroxide, cesium hydroxide and other alkali metal hydroxides; sodium ethoxide, lithium ethoxide, potassium phenoxide and other alkali metal alkoxides and phenoxides; calcium hydroxide, barium hydroxide, strontium hydroxide and other alkali earth metal hydroxides; calcium methoxide, calcium phenoxide and other alkali earth metal alkoxides and phenoxides; magnesium oxide, barium oxide and other alkali earth metal oxides; and triethylamine, dimethylamine, aniline, morpholine, pyridine and other organic amino compounds. In these basic compounds, alkali metal hydroxides are preferably used due to low price and handling with ease. No particular limitation is imposed upon the amount of basic compounds. The amount is usually in the range of 1 to 1,000 moles per mole of the raw material alkylphenol contained in the formed product consisting primarily of alkylcyclohexanol.

Distillation can be carried out by both batch and continuous procedures.

The alkylene oxide addition step mentioned below is carried out by using the high purity alkylcyclohexanol thus obtained to provide alkylcyclohexanol alkylene oxide adduct containing a trace amount or less of alkylphenol.

In the alkylene oxide addition step of the invention, alkylcyclohexanol obtained in the first distillation step reacts with alkylene oxide having 2 to 4 carbon atoms in the presence of an acid catalyst to give alkylcyclohexanol alkylene oxide adduct.

The alkylene oxide having 2 to 4 carbon atoms which can be used in the alkylene oxide addition step includes, for example, ethylene oxide, propylene oxide and butylene oxide. Alkylene oxide can be used singly or as a mixture. When alkylene oxide is used as a mixture, both random and block addition can be carried out. Addition mole numbers of alkylene oxide is in the range of 1 to 5 moles for 1 mole of alkylcyclohexanol.

Alkylene oxide addition mole numbers less than the range increases amount of alkylcyclohexanol which remains unreacted. On the other hand, mole numbers higher than the range increases unfavorably formation of by-products such as dioxane.

The acid catalyst used in the alkylene oxide addition step can be soluble or insoluble in the raw material alkylcyclohexanol used, and both Brønsted acid and Lewis acid can be used for the catalyst. Specific acids include, for example, hydrochloric acid, sulfuric acid, phosphoric acid, boric acid and other mineral acids; formic acid, acetic acid, propionic acid, benzoic acid and other carboxylic acids; sulfate of aluminum, chromium, cobalt and other metals; phosphate of zirconium, iron, manganese and other metals; aluminum chloride, tin tetrachloride, antimony trichloride and other halogenides of metals; BF$_3$, (C$_2$H$_5$)$_3$OBF$_4$, (C$_2$H$_5$)$_3$OBF$_3$ and other fluorinated boron compounds; tungstosilicic acid, tungstophosphoric acid and other hetero polyacids; aluminum oxide, SiO$_4$-Al$_2$O$_3$, zinc oxide. tungsten oxide and other metal oxides; activated clay, zeolite, montmorillonite and other H-type or metal substituted type ion exchangers; and cation exchange resins having a sulfonate group, fluoroalkylsulfonate group, fluorinated alkylsulfonate group and carboxylic acid group. Preferred catalysts are aluminum chloride, tin tetrachloride, antimony trichloride and other metal halogenides, and Lewis acid base catalysts such as BF$_3$, (C$_2$H$_5$)$_3$OBF$_4$, (C$_2$H$_5$)$_3$OBF$_3$ and other fluorinated boron compounds.

The amount of the catalyst used in the process differs depending upon the species of the catalyst and reaction temperature. The amount is usually in the range of 100 to 10,000 ppm by weight for the raw material alkylcyclohexanol. The acid catalyst soluble in the reaction mass can be removed by neutralizing with a basic compound such as alkali metal hydroxide or water-soluble amine and successively washing with water. When the salt is separated the catalyst can be completely removed by filtering off the precipitate and further washing the filtrate with water, when necessary. Further, the catalyst insoluble in the reaction mass can be usually removed by filtration. Further, the catalyst can also be separated by distillation without neutralization operation.

The reaction temperature in the first alkylene oxide addition step is usually in the range of 20 to 120° C., preferably 30 to 70° C. The reaction time is usually in the range of 0.1 to 30 hours, preferably 0.3 to 20 hours. The reaction pressure is usually in the range of gauge pressure 0 to 2 MPa, preferably 0.1 to 0.7 MPa. No particular restriction is imposed upon the reaction procedures. Batch procedure, semi-batch procedure and continuous procedure can be carried out. The alkylcyclohexanol alkylene-oxide adduct obtained in the step is successively used in the second distillation step below.

The object of the second distillation step of the invention is to remove unreacted alkylcyclohexanol, dioxane, aldehyde and low boiling-point by-products of the reaction and to obtain high purity alkylcyclohexanol alkylene oxide adduct. Accordingly, a distillation apparatus equipped, when necessary, with a rectifying column and reflux condenser can be used. Distillation can be carried out at atmospheric pressure or under reduced pressure. High purity alkylcyclohexanol alkylene oxide adduct can be obtained as still residue. The distillation can be carried out both by the batch procedure and continuous procedure. Recovered, unreacted alcohol can be recycled into the alkylene oxide addition step.

The alkylcyclohexanol alkylene oxide adduct obtained in the preparation processes (E) and represented by the formula (1) has a 10 ppm or less content of alkylphenol and alkylphenol alkylene oxide adduct, has a narrow addition distribution essentially consisting of adduct having alkylene oxide addition numbers of 1 to 5, is liquid, and can be used as a material of surface active agents or a raw material of alkylcyclohexanol alkylene oxide adduct having a high addition numbers of alkylene oxide.

Alkylcyclohexanol alkylene oxide adduct of the invention which is represented by the formula (1) has excellent properties as a nonionic surface active agent and can be used for a surfactant by utilizing its dominant penetrating ability, dispersing ability and emulsifying ability. The adduct can be used as an effective ingredient in many fields. Representative fields which can use the adduct include, for example, scouring cleaner, spinning agent, process oil, knitting oil, scotching oil, textile softener, dyeing auxiliaries and other uses in textile industry; deresination disperant for DP, digestion auxiliaries, pitch dispersant in paper making, antifoaming agent, deinking agent, felt cleaner, agent for coated paper and other uses in paper-pulp industry; emulsifier in emulsion polymerization, antistatic agent, antifogging agent and other uses in synthetic rubber and resin industries; emulsifier, solubilizing agent, spreading agent, hydrating agent, dispersant, lubricant and other uses in agricultural chemicals industry; metal cleaner, rust preventive and other uses in metal industry; and garment working agent, kitchen detergent, residence cleaner and other household detergents.

EXAMPLES

Reference Example 1

Synthesis of Nonylphenol Ethylene Oxide Adduct

To a 1,000 ml autoclave equipped with an ethylene oxide inlet tube, 220 g (0.998 mole) of nonylphenol having a branched nonyl group and an ortho/para ratio of 1/9, and 0.55 g of 40% aqueous sodium hydroxide solution (5.5 mmoles of sodium hydroxide) were charged. The reaction system was substituted with nitrogen and thereafter heated to 120° C. Successively the reaction system was evacuated to 50 mmHg and dehydrated for an hour. After dehydration, the system was returned to atmospheric pressure with nitrogen and heated to 150° C. While maintaining the same temperature, 220 g (4.99 moles) of ethylene oxide were charged to the reaction system over 5 hours under the pressure of 0.2 to 0.4 MPa (gauge). After finishing ethylene oxide charge, the reaction mixture was kept at the same temperature for an hour. After cooling, the reaction mixture was neutralized with 0.0.35 g (5.8 mmoles) of acetic acid to obtain 440 g of nonylphenol ethylene oxide adduct. The adduct obtained had an ethylene oxide addition mole numbers of 5.0 for one mole of nonylphenol.

Nonylphenol ethylene oxide adducts having arbitrary addition mole numbers of ethylene oxide were similarly, prepared with similar procedures described above by changing the ratio of ethylene oxide to nonylphenol to be reacted.

Example 1

To a 70 ml autoclave, 20 g (45.4 mmoles, mole numbers of nonylphenoxy skeleton, hereinafter the same shall apply) of nonylphenol ethylene oxide adduct having an ethylene oxide addition mole number of 5.0 and 2.0 g of 5%-ruthenium carbon powder were charged. The reaction system was substituted with nitrogen, successively substituted with hydrogen and heated to 120° C. Hydrogenation reaction was carried out for 6 hours under hydrogen gauge pressure of 5.0 MPa while controlling the pressure by continuously feeding hydrogen so as to maintain the constant pressure. After the reaction, the catalyst was filtered at 70° C. under increased pressure to obtain colorless liquid. As a result of $^1$H and $^{13}$C-NMR, elementary analysis, mass spectrometry and IR spectrum measurement, the liquid was identified as nonylcyclohexanol ethylene oxide adduct having an ethylene oxide addition mole number of 5.0 for nonylcyclohexanol.

The consumed amount of hydrogen during the reaction was 136.6 mmoles and was 3.01 moles per 1 mole of charged nonylphenol ethylene oxide adduct. Nonylphenol ethylene oxide adduct residual in nonylcyclohexanol ethylene oxide adduct was determined by liquid chromatography.

The amount was 120 ppm by weight. Further, nonylcyclohexane formed by hydrogenation decomposition reaction was determined by gas chromatography. The amount was 150 ppm by weight.

Examples 2 and 3

The same reaction and filtration procedures as Example 1 were carried out except that nonylphenol ethylene oxide adduct having the ethylene oxide addition mole numbers shown in Table 1 was used and the reaction was carried out for the time shown in Table 1. Nonylcyclohexanol ethylene oxide adducts having different ethylene oxide addition mole numbers were obtained. Amounts of consumed hydrogen, residual nonylphenol ethylene oxide adduct and nonylcyclohexane are shown in Table 1.

TABLE 1

|  | Example 1 | Example 2 | Example 3 |
|---|---|---|---|
| Ethylene oxide addition mole number | 5.0 | 10.0 | 15.0 |
| Reaction time (hr) | 6 | 6 | 5 |
| Consumed hydrogen (mmole) | 136.6 | 90.8 | 68.2 |
| Mole ratio to nonylphenol ethylene oxide adduct | (3.01) | (3.00) | (3.00) |
| Residual nonylphenol ethylene oxide adduct (ppm by weight) | 120 | 130 | 120 |
| Nonylcyclohexane (ppm by weight) | 150 | 120 | 100 |

Example 4

The same reaction and filtration procedures as Example 1 were carried out except that monoethylene glycol mononoylphenyl ether was used in place of nonylphenol ethylene oxide adduct having an ethylene oxide addition mole number of 5.0 and the catalyst amount was changed to 4.0 g. Monoethylene glycol monononylcyclohexyl ether was obtained.

Consumed hydrogen was 226.8 mmoles which corresponded to 3.00 mole ratio to monoethylene glycol monononylphenyl ether used, residual monoethylene glycol monononylphenyl ether was 100 ppm by weight, and nonylcyclohexane was 100 ppm by weight.

Examples 5~8 and Comparative Example 1

To 70 ml autoclave, 20 g (45.4 mmoles) of nonylphenol ethylene-oxide adduct having an ethylene oxide addition mole number of 5.0 and 2.0 g of powdery 5%-ruthenium alumina were charged. The reaction system was substituted with nitrogen, successively with hydrogen, and heated to 100° C. Hydrogen pressure was respectively controlled to the pressure shown in Table 2. Hydrogenation reaction was carried out for the time and at the temperature shown in Table 2 while feeding hydrogen so as to maintain the hydrogen pressure constant. After the reaction, the catalyst was filtered at 90° C. under increased pressure to obtain nonylcyclohexanol ethylene oxide adduct having an ethylene oxide addition mole number of 5.0. Table 2 shows amounts of consumed hydrogen, residual nonylphenol ethylene oxide adduct and nonylcyclohexane.

As shown in the results of Comparative Example 1, too low hydrogen pressure unfavorably leads to very slow reaction rate.

TABLE 2

|  | Comparative Example 1 | Example 5 | Example 6 |
|---|---|---|---|
| Hydrogen pressure (gauge pressure, MPa) | 0.5 | 5.0 | 7.0 |
| Reaction time (hr) | 30 | 10 | 8 |
| Consumed hydrogen (mmole) | 49.0 | 136.1 | 136.3 |
| Mole ratio to nonylphenol ethylene oxide adduct | (1.08) | (3.00) | (3.00) |
| Residual nonylphenol ethylene oxide adduct (ppm or % by weight) | 63.90% | 150 ppm | 120 ppm |
| Nonylcyclohexane (ppm by weight) | 50 | 100 | 150 |

|  | Example 7 | Example 8 |
|---|---|---|
| Hydrogen pressure (gauge pressure, MPa) | 9.0 | 12.0 |
| Reaction time (hr) | 6 | 6 |
| Consumed hydrogen (mmole) | 136.7 | 136.7 |
| Mole ratio to nonylphenol ethylene oxide adduct | (3.01) | (3.01) |
| Residual nonylphenol ethylene oxide adduct (ppm or % by weight) | 100 ppm | 100 ppm |
| Nonylcyclohexane (ppm by weight) | 150 | 180 |

Examples 9 and Comparative Examples 2 and 3

The same reaction and filtration procedures as Example 5 were carried out except that the reaction temperature and reaction time were employed as shown in Table 3. Nonylcyclohexanol ethylene oxide adduct thus obtained had amounts of consumed hydrogen, residual nonylphenol ethylene oxide adduct and nonylcyclohexane as shown in Table 3.

As shown in the results of Comparative Example 2, too low reaction temperature unfavorably leads to react very slowly. On the other hand, too high reaction temperature is unfavorably liable to cause hydrogenation decomposition.

TABLE 3

|  | Comparative Example 2 | Example 5 | Example 9 | Comparative Example 3 |
|---|---|---|---|---|
| Reaction temperature (° C.) | 30 | 100 | 120 | 180 |
| Reaction Time (hr) | 40 | 10 | 7 | 5 |
| Consumed hydrogen (mmole) | 7.6 | 136.1 | 136.2 | 138.5 |
| Mole ratio to nonylphenol ethylene oxide adduct | (0.17) | (3.00) | (3.00) | (3.05) |
| Residual nonylphenol ethylene oxide adduct (ppm by weight) | 94.50% | 150 ppm | 120 ppm | 120 ppm |
| Nonylcyclohexane (ppm by weight) | 10 ppm or less | 120 ppm | 180 ppm | 0.80% |

Examples 10 and 11

The same reaction and filtration procedures were carried out as Example 1 except that the catalyst, hydrogen pressure, reaction temperature and reaction time were changed as shown in Table 4. Nonylcyclohexanol ethylene oxide adduct was obtained. Amounts of consumed hydrogen, residual nonylphenol ethylene oxide adduct and nonylcyclohexane are shown in Table 4.

TABLE 4

|  | Example 10 | Example 11 |
|---|---|---|
| Catalyst | 5% Rh/C | 5% Rh/Al$_2$O$_3$ |
| Hydrogen pressure (gauge pressure, MPa) | 5.0 | 5.0 |
| Reaction temperature (° C.) | 70 | 70 |
| Reaction time (hr) | 8 | 10 |
| Consumed hydrogen (mmole) | 136.2 | 137.1 |
| Mole ratio to nonylphenol ethylene oxide adduct | (3.00) | (3.02) |
| Residual nonylphenol ethylene oxide adduct (ppm by weight) | 130 | 100 |
| Nonylcyclohexane (ppm by weight) | 160 | 140 |

Example 12

To a 70 ml autoclave, 20 g (45.5 mmoles) of nonylphenol ethylene-oxide adduct having an ethylene oxide addition mole number of 5.0, 4.0 g of wet powder of 5%-ruthenium carbon having a moisture content of 50% by weight and 20 g of ethanol were charged. The system was substituted with nitrogen, thereafter with hydrogen and heated to 60° C. Hydrogen pressure was controlled to the gauge pressure of 6.0 MPa and hydrogenation reaction was carried out at the same temperature for 5 hours while feeding hydrogen so as to maintain the same pressure. After the reaction, the catalyst was filtered at 50° C. and successively water and solvent were removed to obtain a colorless liquid fraction. As a result of determination by $^1$H and $^{13}$C-NMR, elementary analysis, mass spectrometry and IR-spectrum, the liquid was identified as nonylcyclohexanol ethylene oxide adduct having an ethylene oxide addition number of 5.0.

The amount of hydrogen consumed during the reaction was 136.6 mmoles which corresponded to 3.01 mole per one mole of the nonylphenol ethylene oxide adduct charged. The amount of residual nonylphenol ethylene oxide adduct in nonylcyclohexanol ethylene-oxide adduct was determined by liquid chromatography. The amount was 40 ppm by weight. Nonylcyclohexane formed by the hydrogenation decomposition reaction was determined by gas chromatography. The amount was 90 ppm by weight.

Examples 13~17

Nonylphenol ethylene oxide adduct having an ethylene oxide addition mole number shown in Table 5 and Table 6 was used. The reaction, filtration, dehydration and solvent removal were carried out by the same procedures Example 12 except that the reaction time was changed to the time shown in Table 6. Nonylcyclohexanol ethylene oxide adduct having different addition mole numbers of ethylene oxide was obtained. The amounts of consumed hydrogen, residual nonylphenol ethylene oxide adduct and nonylcyclohexane are shown in Table 5 and Table 6.

As clearly shown in Table 5 and Table 6, the reaction was almost completed in 3 hours in any addition mole number of ethylene oxide.

TABLE 5

|  | Example 12 | Example 13 | Example 14 |
|---|---|---|---|
| Ethylene oxide addition mole number | 5.0 | 10.0 | 15.0 |
| Reaction time (hr) | 5 | 5 | 5 |
| Consumed hydrogen (mmole) | 136.6 | 90.8 | 68.2 |
| Mole ratio to nonylphenol ethylene oxide adduct | (3.01) | (3.00) | (3.00) |
| Residual nonylphenol ethylene oxide adduct (ppm by weight) | 40 | 40 | 50 |
| Nonylcyclohexane (ppm by weight) | 90 | 90 | 100 |

TABLE 6

|  | Example 15 | Example 16 | Example 17 |
|---|---|---|---|
| Ethylene oxide addition mole number | 5.0 | 10.0 | 15.0 |
| Reaction time (hr) | 3 | 3 | 3 |
| Consumed hydrogen (mmole) | 136.1 | 90.8 | 68.4 |
| Mole ratio to nonylphenol ethylene oxide adduct | (3.00) | (3.00) | (3.01) |
| Residual nonylphenol ethylene oxide adduct (ppm by weight) | 40 | 45 | 50 |
| Nonylcyclohexane (ppm by weight) | 95 | 90 | 100 |

Example 18

The reaction, filtration, dehydration and solvent removal were carried out by the same procedures as Example 12 except that nonylphenol propylene oxide adduct having a propylene oxide addition mole number of 5.0 was used in place of nonylphenol ethylene oxide adduct having an ethylene oxide addition mole number of 5.0. Nonylcyclohexanol propylene oxide adduct was obtained.

Consumed amount of hydrogen was 117.5 mmoles which corresponded to 3.00 mole ratio to nonylphenol propylene oxide adduct used, the amount of residual nonylphenol propylene oxide adduct was 50 ppm by weight, and the amount of formed nonylcyclohexane was 80 ppm by weight.

Example 19

The reaction, filtration, dehydration and solvent removal were carried out by the same procedures as Example 12 except that n-octylphenol ethylene oxide adduct having an ethylene oxide addition mole number of 5.0 was used in place of nonylphenol ethylene oxide adduct having an ethylene oxide addition mole number of 5.0. n-Octylcyclohexanol ethylene oxide adduct was obtained.

Consumed amount of hydrogen was 141.3 mmoles which corresponded to 3.01 mole ratio to n-octylphenol ethylene oxide adduct used, the amount of residual n-octylphenol ethylene oxide adduct was 50 ppm by weight, and the amount of n-octylcyclohexanol was 95 ppm by weight.

Example 20

The reaction, filtration, dehydration and solvent removal were carried out by the same procedures as Example 12 except that 2.0 g of dried powder of 5%-ruthenium carbon and 2 g of water were used in place of 4.0 g of wet powder of 5%-ruthenium carbon having a moisture content of 50% by weight. Nonylcyclohexanol ethylene oxide adduct was obtained.

Consumed amount of hydrogen was 136.1 mmoles which corresponded to 3.00 mole ratio to nonylphenol ethylene oxide adduct used, the amount of residual nonylphenol ethylene oxide adduct was 40 ppm by weight, and the amount of nonylcyclohexane was 85 ppm by weight.

Comparative Example 4

The reaction, filtration, dehydration and solvent removal were carried out by the same procedures as Example 12 except that 2.0 g of dried powder of 5%-ruthenium carbon was used in place of 4.0 g of wet powder of 5%-ruthenium carbon having a moisture content of 50% by weight. Nonylcyclohexanol ethylene oxide adduct was obtained. The amount of hydrogen consumed during the reaction was 68.1 mmoles which corresponded to a mole ratio of 1.50 to the amount of nonylphenol ethylene oxide adduct charged. The amount of residual nonylphenol ethylene oxide adduct in nonylcyclohexanol ethylene oxide adduct was determined by liquid chromatography. The amount was 50.1% by weight. Further, nonylcyclohexane formed by the hydrogenation decomposition reaction was determined by gas chromatography. The amount was 150 ppm by weight. As clearly shown in those results, when the reaction was carried out in the absence of water, the reaction rate was very low and satisfactory degree of addition could not be obtained.

Example 21

To a 70 ml autoclave, 20 g (45.5 mmoles) of nonylphenol ethylene oxide adduct having an ethylene oxide addition mole number of 5.0, 20 g of dried powder of 5%-ruthenium carbon, and 20 g of cyclohexane were charged. The system was substituted with nitrogen, thereafter with hydrogen and heated to 60° C. Hydrogen pressure was controlled to gauge pressure of 6.0 MPa and hydrogenation reaction was carried out for 3 hours at the same temperature, while continuously feeding hydrogen so as to maintain the same pressure. After the reaction, the catalyst was filtered at 50° C. under increased pressure and the solvent was removed by distillation to obtain a fraction of colorless liquid. Measurement of $^1$H and $^{13}$C-NMR, elementary analysis, mass spectrometry and IR-spectrum analysis identified the liquid as nonylcyclohexanol ethylene oxide adduct having an ethylene oxide addition mole number of 5.0.

The amount of hydrogen consumed during the reaction was 136.1 mmoles which corresponded to 3.00 mole ratio to the nonylphenol ethylene oxide adduct used. Nonylphenol ethylene oxide adduct residual in nonylcyclohexanol ethylene oxide adduct was determined by liquid chromatography. The amount was 60 ppm by weight. Nonylcyclohexane formed by the hydrogenation decomposition reaction was determined by gas chromatography. The amount was 90 ppm by weight.

Comparative Example 5

The reaction, filtration, and solvent removal were carried out by the same procedures as Example 21 except ethanol was used in place of cyclohexane. Nonylcyclohexanol ethylene oxide adduct was obtained. The amount of hydrogen consumed during the reaction was 54.4 mmoles which amount corresponded to a mole ratio of 1.19 to the charged nonylphenol ethylene oxide adduct. The amount of nonylphenol ethylene-oxide adduct residual in the nonylcyclohexanol ethylene oxide adduct was determined by liquid chromatography. The amount was 60.2% by weight. Further, nonylcyclohexane formed by the hydrogenation decomposition reaction was determined by gas chromatography. The amount was 140 ppm by weight. These results clearly show that, when the reaction was carried out by using a solvent other than saturated hydrocarbon, the reaction rate was very low and satisfactory results could not be obtained.

Example 22

The reaction, filtration, dehydration and solvent removal were carried out by the same procedures as Example 21 except that 4.0 g (moisture content was 50% by weight) of wet powder of 5%-ruthenium carbon was used in place of 2.0 g of dried powder of 5%- ruthenium carbon. Nonylcyclohexanol ethylene oxide adduct was obtained.

The amount of consumed hydrogen was 136.1 mmoles which corresponded to a mole ratio of 3.00 to nonylphenol ethylene oxide adduct used, the amount of residual nonylphenol ethylene oxide adduct was 30 ppm by weight, and the amount of nonylcyclohexane was 55 ppm by weight.

Example 23~27

The same reaction, filtration, dehydration and solvent recovery procedures were carried out as Example 22 except that nonylphenol ethylene oxide adduct having an ethylene oxide addition mole number shown in Table 7 and Table 8, was used and reaction was carried out for the time shown in Table 7 and Table 8. Nonylcyclohexanol ethylene oxide adduct which differs in the ethylene oxide addition mole number was obtained. Amounts of consumed hydrogen, residual nonylphenol ethylene oxide adduct and nonylcyclohexane are shown in Table 7 and Table 8.

As clearly shown in Table 7 and Table 8, when a saturated hydrocarbon solvent is used, the reaction rate is very high and the reaction can almost complete within 1.5 hours in any addition mole numbers of ethylene oxide.

TABLE 7

|  | Example 22 | Example 23 | Example 24 |
|---|---|---|---|
| Ethylene addition mole number | 5.0 | 10.0 | 15.0 |
| Ereaction time (hr) | 3 | 3 | 3 |
| Consumed hydrogen (mmole) | 136.1 | 91.1 | 68.2 |
| Mol ratio to nonylphenol ethylene oxide adduct | (3.00) | (3.01) | (3.00) |
| Residual nonylphenol ethylene oxide adduct (ppm by weight) | 40 | 45 | 50 |
| Nonylcyclohexane (ppm by weight) | 55 | 55 | 60 |

TABLE 8

|  | Example 25 | Example 26 | Example 27 |
|---|---|---|---|
| Ethylene oxide addition mole number | 5.0 | 10.0 | 15.0 |
| Reaction time (hr) | 1.5 | 1.5 | 1.5 |
| Consumed hydrogen (mmole) | 136.1 | 90.8 | 68.4 |
| Mol ratio to nonylphenol ethylene oxide adduct | (3.00) | (3.00) | (3.01) |
| Residual nonylphenol ethylene oxide adduct (ppm by weight) | 45 | 45 | 55 |
| Nonylcyclohexane (ppm by weight) | 65 | 60 | 60 |

Example 28

The reaction, filtration and solvent removal were carried out by the same procedures as Example 21 except that cyclohexane was replaced by n-heptane to obtain nonylcyclohexanol ethylene oxide adduct. Amount of consumed hydrogen was 136.6 mmoles which corresponded to a mole ratio of 3.01 to nonylphenol ethylene oxide used, amount of residual nonylphenol ethylene oxide adduct was 120 ppm by weight, and the amount of nonylcyclohexane was 95 ppm by weight.

Example 29

The First Ethylene Oxide Addition Step

To a 1,000 ml autoclave equipped with an ethylene oxide inlet tube, 440 g (2.00 moles) of nonylphenol and 0.66 g (6.6 mmoles as sodium hydroxide) of a 40% aqueous sodium hydroxide solution were charged. The system was substituted with nitrogen and heated to 120° C. Thereafter the system was evacuated to 50 mmHg and dehydration was carried out for an hour under reduced pressure. After the dehydration, the system was returned to atmospheric pressure by feeding nitrogen and heated to 150° C. While maintaining the temperature, 92 g (2.09 moles) of ethylene oxide was charged to the reaction system over 3 hours under increased gauge pressure of 0.2 to 0.4 MPa. The ethylene oxide addition reaction of nonylphenol was thus carried out to react 1.05 moles of ethylene oxide with 1 mole of nonylphenol. After ethylene oxide charge, the reaction mixture was kept at the same temperature for an hour, cooled and neutralized the catalyst with 0.47 g (7.0 mmoles) of acetic acid to obtain 532 g of colorless liquid. The liquid was analyzed with liquid chromatography. The liquid contained, 1.2% by weight of nonylphenol, 96.7% by weight of one molar ethylene oxide adduct of nonylphenol, and 2.1% by weight of two molar ethylene oxide adduct of nonylphenol, respectively.

Hydrogenation Step

To a 1,000 ml autoclave, 520 g (1.95 moles) of the formed product obtained in the first ethylene oxide addition step and composed primarily of nonylphenol one molar ethylene oxide adduct, and 30 g of powdery 5%-ruthenium carbon were charged. The system was substituted with nitrogen, successively with hydrogen and heated to 120° C. Hydrogen pressure was controlled to gauge pressure of 5.0 MPa, and the hydrogenation reaction was carried out for 6 hours at the same temperature while continuously feeding hydrogen so as to maintain the same pressure. After the reaction, the catalyst was filtered at 70° C. under increased pressure to obtain 532 g of colorless liquid. The amount of hydrogen consumed over the reaction was 5.88 moles which corresponded to a molar ratio of 3.01 to nonylphenol ethylene oxide adduct charged. As a result of measurement on $^1$H and $^{13}$C-NMR, mass spectrometry and elementary analysis, the liquid was composed primarily of one molar ethylene oxide adduct of nonylcyclohexanol and most of nonylphenol and its ethylene oxide adduct were found to become hydrogenation products. As a result of liquid chromatography, the sum of residual nonylphenol and nonylphenol ethylene oxide adduct was 150 ppm by weight.

Distillation Step

By using a batch type vacuum distillation apparatus equipped with a rectifying column and reflux condenser, 520 g of the colorless liquid obtained in the hydrogenation step and composed primarily of one molar ethylene oxide adduct of nonylcyclohexanol was distilled under reduced pressure. As an initial fraction, 10.3 g of the fraction composed mainly of nonylcyclohexanol was obtained. As a main fraction, 462.2 g of the fraction composed mainly of one molar ethylene oxide adduct of nonylcyclohexanol. The remainder was disposed as still residue. According to the analysis by liquid chromatography, the main fraction was one molar ethylene oxide adduct of nonylcyclohexanol which contains 0.06% by weight of nonylcyclohexanol. The sum of nonylphenol and nonylphenol ethylene oxide adduct was 0.1 ppm by weight or less.

The Second Ethylene Oxide Addition Step

To a 1,000 ml autoclave equipped with an ethylene oxide inlet tube, 270 g (1.00 mole) of one molar ethylene oxide adduct of nonylcyclohexanol, obtained in the distillation step and 0.67 g (6.7 mmoles as sodium hydroxide) of a 40% aqueous solution of sodium hydroxide were charged. The reaction system was substituted with nitrogen, heated to 120° C., successively evacuated to 50 mmHg and dehydrated for an hour under reduced pressure. After dehydration, the system was returned to atmospheric pressure by feeding nitrogen, and heated to 150° C. Successively ethylene oxide addition reaction of one molar ethylene oxide adduct of nonylcyclohexanol was carried out by feeding 265 g (6.02 moles) of ethylene oxide into the reaction system over 6 hours under increased gauge pressure of 0.2 to 0.4 MPa while maintaining the same temperature. After ethylene oxide feeding, the reaction system was kept at the same temperature for an hour, cooled and neutralized the catalyst with 0.42 g (7.0 mmoles) of acetic acid to obtain nonylcyclohexanol ethylene oxide adduct as colorless liquid. According to analysis by liquid chromatography, the colorless liquid was nonylcyclohexanol ethylene oxide adduct having an average ethylene oxide addition mole number of 7.0. The colorless liquid had 0.1 ppm by weight or less in the sum of nonylphenol and nonylphenol ethylene oxide adduct.

Example 30

The First Ethylene Oxide Addition Step

The same procedures were carried out as Example 29.

Hydrogenation Step

The same procedures were carried out as Example 29 except that 5%-rhodium alumina was used in place of 5%-ruthenium carbon and the reaction was carried out at 100° C. After the reaction, the catalyst was filtered at 70° C. under increased pressure to obtain 532 g of colorless liquid consisting primarily of one molar ethylene oxide adduct of nonylcyclohexanol. Amount of hydrogen consumed during the reaction was 5.86 moles which corresponded 3.01 mole ratio to nonylphenol ethylene oxide adduct charged.

$^1$H-NMR measurement proved that most of nonylphenol and nonylphenol ethylene oxide adduct was hydrogenated. The residual amount of nonylphenol and nonylphenol ethylene oxide adduct was measured by liquid chromatography. The sum of residual amount was 130 ppm by weight.

Distillation Step

The same procedures as Example 29 were carried out. The main fraction was primarily composed of ethylene oxide one molar adduct of nonylcyclohexanol and was obtained in an amount of 458.9 g . According to the analysis by liquid chromatography, the main fraction was one molar ethylene oxide adduct of nonylcyclohexanol containing 0.07% by weight of nonylcyclohexanol. The sum of nonylphenol and nonylphenol ethylene oxide adduct was 0.1 ppm by weight or less.

The Second Ethylene Oxide Addition Step

The same procedures were carried out as Example 29.

Nonylcyclohexanol ethylene-oxide adduct having an average ethylene oxide addition mole number of 7.0 was obtained. According to the analysis by liquid chromatography, the sum of nonylphenol and nonylphenol ethylene oxide adduct was 0.1 ppm by weight or less.

Example 31

The First Ethylene Oxide Addition Step

The same procedures were carried out as Example 29.

Hydrogenation Step

The same procedures as Example 29 were carried out except that Raney nickel was used in place of 5%-ruthenium carbon, 200 g of ethanol was added as a solvent, reaction temperature was 100° C., hydrogen gauge pressure was 8.0 MPa, and reaction time was 8 hours. After the reaction, the catalyst was filtered at 70° C. under increased pressure, and distilling off ethanol with a thin film still to obtain 532 g colorless liquid principally composed of one molar ethylene oxide adduct of nonylcyclohexanol. The amount of hydrogen consumed during the reaction was 5.78 moles which corresponded 2.97 mole ratio to nonylphenol ethylene oxide adduct charged.

As a result of $^1$H-NMR measurement, nonylphenol and nonylphenol ethylene oxide adduct are revealed to be mostly hydrogenated. Residual amount of nonylphenol and nonylphenol ethylene oxide adduct were determined by liquid chromatography. The sum of these amounts was 320 ppm by weight.

Distillation Step

The same procedures as Example 29 were carried out. The main fraction, 447.3 g of a fraction principally consisting of one molar ethylene oxide adduct of nonylcyclohexanol was obtained. Analysis by liquid chromatography revealed that the main fraction was one molar ethylene oxide adduct of nonylcyclohexanol containing 0.05% by weight of nonylcyclohexanol. The amount of nonylphenol and nonylphenol ethylene oxide adduct was 0.1 ppm by weight or less.

The Second Ethylene Oxide Addition Step

The same procedures as Example 29 were carried out to obtain nonylcyclohexanol ethylene oxide adduct having an average ethylene oxide addition mole number of 7.0. As a result of liquid chromatography measurement, the sum of nonylphenol and nonylphenol ethylene oxide adduct was 0.1 ppm by weight or less.

Comparative Example 6

The First Ethylene Oxide Addition Step

The same procedures as Example 29 were carried out.

Hydrogenation Step

The same procedures as Example 29 were carried out.

Distillation Step

The procedures were omitted.

The Second Ethylene Oxide Addition Step

The same procedures as Example 29 were carried out for reacting 270 g of the reaction product which was obtained in the hydrogenation step and composed primarily of one molar ethylene oxide adduct of nonylcyclohexanol with 265 g of ethylene oxide. Nonylcyclohexanol ethylene oxide adduct thus obtained was analyzed with liquid chromatography. The product contained 80 ppm by weight or less in the sum of nonylphenol and nonylphenol ethylene oxide adduct.

Comparative Example 7

The same procedures as the first ethylene oxide addition step of Example 29 were carried out except that the amount of ethylene oxide was changed to 61 g (1.38 moles). That is, 0.69 mole of ethylene oxide was reacted with 1 mole of nonylphenol. Colorless liquid thus obtained was analyzed with liquid chromatography. The liquid contained 27.3% by weight of nonylphenol, 72.7% by weight of one molar ethylene oxide adduct, and trace amount of two molar ethylene oxide adduct of nonylphenol, respectively. The reaction product unfavorably formed a large amount of nonylcyclohexanol in the next hydrogenation step.

Comparative Example 8

The same reaction and neutralization procedures as the first ethylene oxide addition step of Example 29 were carried out except that 132 g (3.00 moles) of ethylene oxide was reacted in the step. That is, 1.5 moles of ethylene oxide were reacted with 1 mole of nonylphenol. Colorless liquid thus obtained was analyzed with liquid chromatography. No nonylphenol was contained in the liquid and the amounts of nonylphenol ethylene oxide adduct contained were 49.0% by weight in one molar adduct, 48.5% by weight in two molar adduct, and 2.5% by weight in 3 molar adduct, respectively.

The reaction product unfavorably generated a large amount of two moles or more ethylene oxide adducts of nonylcyclohexanol in the next hydrogenation step.

Example 32

Hydrogenation Step

To a 1,000 ml autoclave, 506.8 g (2.30 moles) of nonylphenol and 30 g of 5%-ruthenium carbon powder were charged. The reaction system was substituted with nitrogen and thereafter with hydrogen and heated to 120° C. Hydrogen pressure was controlled to gauge pressure of 5.0 MPa, and hydrogenation reaction was carried out for 6 hours at the same temperature, while continuously feeding hydrogen so as to maintain the same pressure. After the reaction, the catalyst was filtered at 70° C. under increased pressure to obtain 521.0 g of colorless liquid. Amount of consumed hydrogen during the reaction was 6.94 moles which corresponded to 3.02 mole ratio to nonylphenol charged. Measurement by $^1$H and $^{13}$C-NMR, mass spectrometry and elementary analysis revealed that the liquid consisted primarily of nonylcyclohexanol and most of nonylphenol were hydrogenated. Amount of remainder nonylphenol was determined with liquid chromatography. The amount was 150 ppm by weight in the sum.

The First Distillation Step

With a batch type reduced pressure distillation apparatus equipped with a rectifying column and reflux condenser, 510 g of colorless liquid obtained in the hydrogenation step was distilled under reduced pressure. Initial fraction was 5.3 g and composed of nonylcyclohexanol containing low boiling fraction. Main fraction was 480 g . The main fraction was analyzed by liquid chromatography and was revealed to be nonylcyclohexanol. The amount of nonylphenol was 0.1 ppm by weight or less by liquid chromatography.

Alkylene Oxide Addition Step

To a 1,000 ml autoclave equipped with an ethylene oxide inlet tube, 453 g (2.00 moles) of nonylcyclohexanol, and 2.5 g of a catalyst $(C_2H_5)_2OBF_3$ were charged. The system was substituted with nitrogen and warmed to 30° C. While maintaining the reaction temperature at 40 to 60° C., 176 g (4.0 moles; 2.0 moles per mole of charged nonylcyclohexanol) of ethylene oxide was charged to the system under gauge pressure of 0.2 to 0.4 MPa, over 1.5 hours to carry out the ethylene oxide addition reaction of nonylcyclohexanol. That is, 2.0 moles of ethylene oxide was reacted with 1 mole of nonylcyclohexanol. After ethylene oxide charge, the system was further kept at the same temperature for an hour. After cooling, the reaction mixture was neutralized with a 25% aqueous sodium hydroxide solution and the catalyst was removed by washing twice with water. A colorless liquid thus obtained was 629.2 g. The liquid was analyzed by liquid chromatography. The content of unreacted nonylcyclohexanol was 24.1% by weight, formed one molar ethylene oxide adduct of nonylcyclohexanol was 16.9% by weight, two molar adduct of 17.5% by weight, 3 molar adduct of 16.0% by weight, 4 molar adduct of 12.3% by weight, 5 molar adduct of 7.7% by weight, and 5 or more molar adduct of 5.5% by weight, respectively. As a result of liquid chromatography, the sum of nonylphenol and nonylphenol ethylene oxide adduct was less than 0.1 ppm by weight.

The Second Distillation Step

With a batch type vacuum distillation apparatus equipped with a rectifying column and reflux condenser, 610 g of colorless liquid obtained in the alkylene oxide addition step was distilled under reduced pressure. 147.3 g of unreacted nonylcyclohexanol was distilled out and 458.1 g of residue was residual in the bottom. The residue was analyzed by gas chromatography and no nonylcyclohexanol was detected. Average addition mole number calculated from measured hydroxyl value was 3.00. Hydroxyl value was measured in accordance with JIS K-0070.

Example 33

Hydrogenation Step

The same procedures as Example 32 were carried out except that 5%-rhodium alumina was used in place of 5%-ruthenium carbon and the reaction temperature was changed to 100° C. After the reaction, the catalyst was filtered at 70° C. under increased pressure to obtain 521.0 g of colorless liquid consisting primarily of nonylcyclohexanol. $^1$H-NMR measurement revealed that most of nonylphenol was hydrogenated. The sum of residual nonylphenol was 170 ppm by weight by liquid chromatography.

Distillation Step

The same procedures as Example 32 were carried out. The initial fraction was 7. g and composed of nonylcyclohexanol containing low boiling fraction. Main fraction was 475 g and was a nonylcyclohexanol fraction. The main fraction was revealed to be nonylcyclohexanol by analysis with liquid chromatography. The amount of nonylphenol was less than 0.1 ppm by weight by liquid chromatography.

Alkylene Oxide Addition Step

The same procedures as Example 32 were carried out except that ethylene oxide feeding amount was 132 g (3.00 moles; 1.5 moles per mole of nonylcyclohexanol charged). After cooling, the reaction mass was neutralized 25% aqueous sodium hydroxide solution and the catalyst was removed by washing twice with water to obtain 585.6 g of colorless liquid. Liquid chromatography analysis found 21.2% by weight of unreacted nonylcyclohexanol, 21.9% by weight of one molar adduct, 20.9% by weight of two molar adduct, 15.9% by weight of three molar adduct, 10.3% by weight of four molar adduct, 7.3% by weight of five molar adduct, and 2.5% by weight of six or more molar adduct, respectively. Liquid chromatography measurement revealed that the sum of nonylphenol and nonylphenol ethylene oxide adduct was 0.1 ppm by weight or less.

The Second Distillation Step

With a batch type vacuum distillation apparatus equipped with a rectifying column and reflux condenser, 500 g of colorless liquid obtained in the alkylene oxide addition step was distilled under reduced pressure to distil off 106.2 g of unreacted nonylcyclohexanol and to obtain 390.8 g of residue in the bottom. The residue was analyzed by gas chromatography. No nonylcyclohexanol was detected. The average addition mole number calculated from a hydroxyl value measured was 2.06.

Example 34

Hydrogenation Step

The same reaction procedures as Example 32 were carried out except that 5%-palladium carbon was used in place of 5%-ruthenium carbon, reaction temperature was 100° C., hydrogen gauge pressure was 8.0 MPa and reaction time was 8 hours. After finishing the reaction, the catalyst was hot filtered at 70° C. under reduced pressure to obtain 520.8 g of colorless liquid consisting primarily of nonylcyclohexanol. Amount of hydrogen consumed during the reaction was 6.95 moles which amount corresponded to a mole ratio of 3.02 to nonylphenol charged. $^1$H-NMR measurement revealed that most of nonylphenol was hydrogenated. The residual nonylphenol was 190 ppm by weight by liquid chromatography.

Distillation Step

The same procedures as Example 32 were carried out. Initial fraction was 4.5 g and was nonylcyclohexanol containing low boiling fraction. Main fraction was 477 g and composed of nonylcyclohexanol. The main fraction was analyzed by liquid chromatography. The fraction was nonylcyclohexanol. According to liquid chromatography, the amount of nonylphenol was 0.1 ppm by weight or less.

Alkylene Oxide Addition Step

The same procedures as Example 32 were carried out except that feed amount of ethylene oxide was 264.5 g (6.00 moles: 3.0 mole ratio to charged cyclohexanol). After cooling, the reaction mass was neutralized 25% aqueous sodium hydroxide solution, and the catalyst was removed by washing twice with water to obtain 717.2 g of colorless liquid. Liquid chromatographic analysis revealed that unreacted nonylcyclohexanol was 18.1% by weight, formed one mole ethylene oxide adduct of nonylcyclohexanol was 13.6% by weight, two molar adduct was 17.4% by weight, 3 molar adduct was 16.5% by weight, 4 molar adduct was 15.3% by weight, 5 molar adduct was 12.1% by weight, and 6 or more molar adduct was 7.0% by weight, respectively. As a result of liquid chromatographic determination, the sum of nonylphenol and nonylphenol ethylene oxide adduct was 0.1 ppm by weight or less.

The Second Distillation Step

With a batch type vacuum distillation apparatus equipped with a rectifying column and reflux condenser, 500 g of colorless liquid obtained in the alkylene oxide addition step and was distilled under reduced pressure, 90.8 g of unreacted nonylcyclohexanol was distilled off and 406.1 g of residue was obtained in the bottom. As a result of gas chromatography, no nonylcyclohexanol was detected from the residue. The average addition mole number calculated from the hydroxyl value was 4.20.

Example 35

Hydrogenation Step

In Example 32, the reaction was carried out by using 603.6 g (2.3 moles) of n-dodecylphenol in place of the raw material nonylphenol, using Raney nickel in place of 5%-ruthenium carbon powder, adding 200 g of ethanol as a solvent and at a reaction temperature of 100° C. and for a reaction time of 8 hours. After the reaction, the catalyst was filtered at 70° C. under increased pressure, ethanol was distilled off with a thin film evaporator to obtain 617.7 g of colorless liquid consisting primarily of n-dodecylcyclohexanol. The amount of hydrogen consumed during the reaction was 6.99 moles which corresponded to a mole ratio of 3.04 to dodecylphenol charged. As a result of $^1$H-NMR measurement, most of n-dodecylphenol was found to be hydrogenated. Residual n-dodecylphenol was determined by liquid chromatography, and the amount of residual n-dodecylphenol was 145 ppm by weight.

The First Distillation Step

The same procedures as Example 32 were carried out except that 600 g of n-dodecylcyclohexanol obtained in the hydrogenation step was used. An initial fraction composed of n-dodecylcyclohexanol and a low boiling fraction was 6.3 g, and a main fraction composed of n-dodecylcyclohexanol was 566.8 g . The main fraction was analyzed by liquid chromatography. The fraction was n-dodecylcyclohexanol and n-dodeylphenol content was 0.1 ppm by weight or less.

Alkylene Oxide Addition Step

The same reaction procedures Example 32 were carried out except that 537.0 g (2.0 moles) of dodecylcyclohexanol was charged. After cooling, the reaction mass was neutralized 25% aqueous sodium hydroxide solution, and the catalyst was removed by washing twice with water to obtain 713.4 g of colorless liquid. The liquid was analyzed by liquid chromatography. The liquid contained 29.4% by weight of unreacted dodecylcyclohexanol, 16.7% by weight of formed one molar ethylene oxide adduct of dodecylcyclohexanol, 17.4% by weight of two molar adduct, 15.3% by weight of three molar adduct, 12.7% by weight of four molar adduct, 5.9% by weight of five molar adduct, and 2.6% by weight of six or more molar ethylene oxide adduct of dodecylcyclohexanol. As a result of liquid chromatography, the sum of dodecylphenol and dodecylphenol ethylene oxide adduct was 0.1 ppm by weight or less.

The Second Distillation Step

With a batch type vacuum distillation apparatus equipped with a rectifying column and reflux condenser, 500 g of colorless liquid obtained in the alkylene oxide addition step and consisting of dodecylcyclohexanol ethylene oxide adduct was distilled under reduced pressure, and 147.4 g of unreacted dodecylcyclohexanol was distilled off and 348.9 g of residue was obtained in the bottom. The residue was analyzed by gas chromatography. As a result, no dodecylcyclohexanol was detected. The average addition mole number calculated from the measured hydroxyl value was 3.28.

Example 36

Hydrogenation Step

The same procedures were carried out was Example 32. After the reaction, the catalyst was filtered at 70° C. under increased pressure to obtain 520.8 g of colorless liquid. The amount of hydrogen consumed during the reaction was 6.94 moles which corresponded to a mole ratio of 3.02 to nonylphenol charged. As a result of $^1$H-NMR measurement, most of nonylphenol was found to be hydrogenated. The residual amount of nonylphenol was determined by liquid chromatography. The sum of residual amount was 165 ppm by weight.

Distillation Step

The same procedures as Example 32 were carried out. As an initial fraction, 4.3 g of nonylcyclohexanol fraction containing a low boiling fraction was obtained. A s a main fraction, 470 g of nonylcyclohexanol fraction was obtained. The main fraction was analyzed by liquid chromatography. The liquid was nonylcyclohexanol, and nonylphenol content was 0.1 ppm by weight or less.

Alkylene Oxide Addition Step

The same procedures as Example 32 were carried out except that 232.3 g (4.0 moles) of propylene oxide was used in place of ethylene oxide. After cooling, the reaction mass was neutralized 25% aqueous sodium hydroxide solution and the catalyst was removed by washing twice with water to obtain 685.2 g of colorless liquid. The liquid was analyzed by liquid chromatography. The liquid contained 27.9% by weight of unreacted nonylcyclohexanol, 15.5% by weight of formed one molar propylene oxide adduct of nonylcyclohexanol, 17.2% by weight of two molar adduct, 15.6% by weight of three molar adduct, 12.7% by weight of four molar adduct, 6.7% by weight of five molar adduct, and 4.4% by weight of six or more molar propylene oxide adduct of nonylcyclohexanol. As a result of liquid chromatographic analysis, the sum of nonylphenol and nonylphenol propylene oxide adduct was 0.1 ppm by weight or less.

The Second Distillation Step

With a batch type vacuum distillation apparatus equipped with a rectifying column and reflux condenser, 500 g of colorless liquid obtained in the alkylene oxide addition step was distilled under reduced pressure to distil off 139.1 g of unreacted nonylcyclohexanol and 356.7 g of still residue liquid was obtained in the bottom. The residue was analyzed by gas chromatography. No nonylcyclohexanol was detected. The average addition mole number calculated from the measured hydroxyl value was 3.45.

Example 37

The Second Alkylene Oxide Addition Step

To a 1,000 ml autoclave equipped with an ethylene oxide inlet tube, 352.5 g (1.0 mole: average addition mole number of 3.00) of nonylcyclohexanol ethylene oxide adduct obtained in the second distillation step of Example 32 and 0.67 g (6.7 mmoles as sodium hydroxide) of a 40% aqueous sodium hydroxide solution were charged. The reaction system was substituted with nitrogen, heated to 120° C., successively evacuated to 50 mmHg and dehydrated for an hour under reduced pressure. After dehydration, the system was returned to atmospheric pressure by feeding nitrogen and heated to 150° C. While maintaining the temperature, 308.4 g (7.0 moles) of ethylene oxide was fed into the system during 3 hours at gauge pressure of 0.2 to 0.4 MPa to carry out ethylene oxide addition reaction of nonylcyclohexanol ethylene oxide adduct. After finishing the ethylene oxide charge, the reaction mass was further heated at the same temperature for an hour, cooled and neutralized the catalyst with 0.42 g (7.0 mmoles) of acetic acid to obtain 661.6 g of nonylcyclohexanol ethylene oxide adduct as colorless liquid. According to hydroxyl value measurement, the liquid was nonylcyclohexanol ethylene oxide adduct having an average ethylene oxide addition mole number of 9.99. As a result of liquid chromatography, the sum of nonylphenol and nonylphenol ethylene oxide adduct was 0.1 ppm by weight or less.

Example 38

The Second Alkylene Oxide Addition Step

To a 1,000 ml autoclave equipped with an ethylene oxide inlet tube, 264.4 g (0.75 mole) of nonylcyclohexanol ethylene oxide adduct which was obtained in the second distillation step of Example 32 and had an average addition mole number of 3.00, and 0.67 g (6.7 mmoles as sodium hydroxide) of 40% aqueous sodium hydroxide solution were charged. The reaction system was substituted with nitrogen, heated to 120° C., successively evacuated to 50 mmHg, and dehydrated for an hour under reduced pressure. After dehydration, the reaction system was returned to atmospheric pressure by feeding nitrogen and heated to 150° C. While maintaining the temperature, 484.6 g (11.0 moles) of ethylene oxide was fed into the reaction system over 4 hours under gauge pressure of 0.2 to 0.4 MPa to carry out ethylene oxide addition reaction of nonylcyclohexanol ethylene oxide adduct. After the ethylene oxide feed, the reaction system was further heated at the same temperature for an hour, cooled, neutralized the catalyst with 0.42 g (7.0 mmoles) of acetic acid to obtain 750.7 g of nonylcyclohexanol ethylene oxide adduct as colorless liquid. According to hydroxyl value measurement, the adduct obtained had an average ethylene oxide addition mole number of 14.05. As a result of liquid chromatography, the sum of nonylphenol and nonylphenol ethylene oxide adduct was 0.1 ppm by weight or less.

Comparative Example 9

The same alkylene oxide addition step as the alkylene oxide addition step of Example 32 were carried out without the first distillation step. As a result, the reaction mass contained 25.7% by weight of unreacted nonylcyclohexanol, 16.7% by weight of formed ethylene oxide one molar adduct of nonylcyclohexanol, 17.1% by weight of 2 molar adduct, 15.7% by weight of three molar adduct, 11.6% by weight of four molar adduct, 7.7% by weight of five molar adduct, 5.5% by weight of six molar or more adduct of ethylene oxide of nonylcyclohexanol, respectively. The unreacted nonylcyclohexanol was removed according to the second distillation step of the Example 32. According to hydroxyl value measurement, the residue in the bottom had an average ethylene oxide addition mole number of 3.10. As a result of liquid chromatography, the sum of nonylphenol and nonylphenol ethylene oxide adduct was 110 ppm by weight.

Comparative Example 10

The same reaction and catalyst removal procedures as the alkylene oxide addition step of Example 32 were carried out except that 226.5 g (1.00 mole) of nonylcyclohexanol was used, 308.4 g (7.00 moles) of ethylene oxide was reacted, and reaction time was 8 hours. As a result, 534.5 g of white solid was obtained at room temperature. As a result of liquid chromatography analysis, the white solid contained 2.1% by weight of unreacted nonylcyclohexanol, 5.7% by weight of formed ethylene oxide one molar adduct of nonylcyclohexanol, 6.2% by weight of 2 molar adduct, 7.9% by weight of three molar adduct, 8.2% by weight of four molar adduct, 8.8% by weight of five molar adduct, 9.2% by weight of six molar adduct, 9.6% by weight of seven molar adduct, 8.9% by weight of 8 molar adduct, 8.3% by weight of nine molar adduct, 6.8% by weight of ten molar adduct, 6.1% by weight of eleven molar adduct, and 7.9% by weight of twelve or more molar adduct of ethylene oxide of nonylcyclohexanol, respectively. The white solid was analyzed by gas chromatography and was detected 3.2% by weight of dioxane and 1.1% by weight of other low boiling compounds.

Comparative Example 11

To a 1,000 ml autoclave equipped with an ethylene oxide inlet tube, 226.5 g (1.0 mole) of nonylcyclohexanol and 0.67 g (6.7 mmoles as sodium hydroxide) of 40% aqueous sodium hydroxide solution were charged. The reaction system was substituted with nitrogen, heated to 120° C., successively evacuated to 50 mmHg, and carry out dehydration for an hour under reduced pressure. After dehydration, the system was returned to atmospheric pressure by feeding nitrogen, and heated to 150° C. While maintaining the temperature, 396.5 g (9.0 moles) of ethylene oxide was fed into the reaction system over 3 hours under gauge pressure of 0.2 to 0.4 MPa to carry out ethylene oxide addition reaction of nonylcyclohexanol. After finishing ethylene oxide charge, the reaction system was further kept at the same temperature for an hour and the catalyst was neutralized after cooling with 0.42 g (7.0 mmoles) of acetic acid to obtain 623.4 g of nonylcyclohexanol ethylene oxide adduct as white solid at room temperature. The white solid was analyzed by liquid chromatography. The solid contained 38.8% by weight of unreacted nonylcyclohexanol, 0.5% by weight of formed one molar ethylene oxide adduct of nonylcyclohexanol, 1.1% by weight of two molar adduct, 1.6% by weight of three molar adduct, 2.3% by weight of four molar adduct, 3.4% by weight of five molar adduct, 4.3% by weight of six molar adduct, 5.2% by weight of seven molar adduct, 6.3% by weight of eight molar adduct, 7.4% by weight of nine molar adduct, 6.6% by weight of ten molar adduct, 5.8% by weight of eleven molar adduct, and 4.7% by weight of twelve molar adduct, 4.1% by weight of thirteen molar adduct, 3.2% by weight of fourteen molar adduct, and 4.7% by weight of fifteen or more molar adduct.

As mentioned above, when ethylene oxide addition reaction is carried out in the presence of a base catalyst alone, a large amount of unreacted nonylcyclohexanol remains, mole distribution of ethylene oxide addition becomes considerably broad, and high molar adduct increases. Thus the reaction product unfavorably becomes a solid.

Hereinafter illustrated tests were carried out in order to prove that alkylcyclohexanol alkylene oxide adducts of the invention can be applied to various uses.

Reference Example 2

To a 1,000 ml autoclave equipped with an ethylene oxide inlet tube, 220 g (0.998 moles) of nonylphenol having a branched mixture of nonyl group and an ortho/para ratio of 1/9 and 0.83 g (8.3 mmoles as sodium hydroxide) of 40% aqueous sodium hydroxide solution were charged. The reaction system was substituted with nitrogen, heated to 120° C., successively evacuated to 50 mmHg, and dehydrated for an hour under reduced pressure. After the dehydration, the reaction system was returned to atmospheric pressure by feeding nitrogen and heated to 150° C. While maintaining the temperature, 440 g (9.99 moles) of ethylene oxide was fed to the reaction system over 8 hours under increased gauge pressure of 0.2 to 0.4 MPa to carry out ethylene oxide addition reaction of nonylphenol. After ethylene oxide charge, the reaction system was further kept at the same temperature for an hour. After cooling the reaction system, the reaction system was neutralized with 0.52 g (8.7 mmoles) of acetic acid to obtain 660 g of nonylphenol ethylene oxide adduct. Nonylphenol ethylene oxide adduct thus obtained had an average ethylene oxide addition mole number of 10.0.

Successively, to a 1,000 ml autoclave, 200 g (302.6 mmoles) of nonylphenol ethylene oxide adduct having an ethylene oxide addition mole number of 10.0, and 20.0 g of powdery 5%-ruthenium carbon were charged. The reaction system was substituted with nitrogen, successively with hydrogen, and heated to 120° C. The hydrogen pressure was controlled to gauge pressure of 5.0 MPa, and the hydrogenation reaction was carried out for 6 hours at the same temperature while continuously feeding hydrogen so as to maintain the pressure constant. After the reaction, the catalyst was filtered at 70° C. under increased pressure to obtain colorless liquid.

As a result of $^1H$- and $^{13}C$-NMR, elementary analysis, mass spectrometry and IR spectrum measurement, the liquid was identified as nonylcyclohexanol ethylene oxide adduct having an ethylene oxide addition mole number of 10.0 to nonylcyclohexanol.

The consumed amount of hydrogen during the reaction was 914.0 mmoles which amount corresponded to 3.02 mole ratio to nonylphenol ethylene oxide adduct charged. Further, the amount of nonylphenol ethylene oxide adduct remaining in the nonylcyclohexanol ethylene oxide adduct was determined by liquid chromatography. The amount was 120 ppm by weight. Further, nonylcyclohexane formed by hydrogenation decomposition reaction was determined by gas chromatography. The amount was 10 ppm by weight.

With a Model-B viscosimeter, viscosity was measured at 25° C. on nonylcyclohexanol ethylene oxide adduct which was obtained in the present Reference Example 2 and had an ethylene oxide addition mole number of 10 and on intermediate product nonylphenol ethylene oxide adduct having an ethylene oxide addition mole number of 10. The former viscosity was 210 cps and the latter viscosity was 250 cps. Nonylcyclohexanol ethylene oxide adduct had lower viscosity.

Reference Example 3

The same procedures as Reference Example 2 were carried out to obtain nonylcyclohexanol ethylene oxide adduct having an ethylene oxide addition mole number of 6.0.

Reference Example 4

The same procedures as Reference Example 2 were carried out. Nonylcyclohexanol ethylene oxide adduct having an ethylene oxide addition mole number of 30.0 was obtained.

Test Example 1

Fiber Washing Test

As an artificial soil, a mixture of 23.6 g of Kanto clay loam, 0.4 g of carbon black, 56.2 g of synthetic sebum, and 4 kg carbon tetrachloride was used. Synthetic sebum composed of following ingredients;

Palmitic acid 5.6 g, stearic acid 2.8 g, oleic acid 5.6 g, linolic acid 2.8 g, coconut oil 8.4 g, olive oil 11.2 g, paraffin (m.p. 48~50° C.) 5.6 g, spermaceti 8.6 g, squalene 2.8 g, and cholesterol 2.8 g.

The above artificial soil was vigorously stirred with a homomixer in the bath. A standard cotton fabric (JIS L-0803) was dipped into the bath with a continuous automatic soiling machine. The soiled fabric was subjected to natural drying for 3 weeks and successively cut into dimensions of 10 cm square to prepare artificially soiled fabric.

Terg-O-Tometer was used for the detergency test. Washing was carried out at 30° C. for 10 minutes by immersing four soiled fabrics in 1 liter of 0.25% by weight of aqueous solution of nonylcyclohexanol ethylene oxide adduct prepared in Reference Example 2. After washing, rinsing was carried out twice with one liter each of pure water for 3 minutes each. After subjecting the test fabric to air-drying, successively to ironing, surface reflectance of the fabric was measured with a color difference meter for used in colorimetry. Detergency (D) was calculated from the following equation.

$$D(\%)=[1-(Ro-Rw)/(Ro-Rs)]\times 100$$

wherein Rw, Rs and Ro are surface reflectance of washed fabric, soiled fabric and original white fabric, respectively. Detergency was 84%, which illustrated good washing ability.

Test Example 2

Metal Washing Test

A test piece was prepared by coating fiber grease on a wrought iron plate. To 96.0 g of water, 3.0 g of sodium carbonate and 1.0 g of nonylcyclohexanol ethylene oxide adduct prepared in Reference Example 2 was added and warmed to 40° C. The test piece was washed for 10 minutes by moving up and down the test piece in the solution. Weight of the test piece was measured and detergency (D) was calculated from the following equation.

$$D(\%)=[1-(Ww-Wo)/(Ws-Wo)]\times 100$$

wherein Ww, Ws, and Wo are weight of test piece after washing, weight of test piece before washing and weight of test piece before coating the fiber grease, respectively.

Detergency was 99.2%, which illustrated good washing ability.

Test Example 3

Tableware Washing Test

Test was carried out by washing a glass piece adhered with model soil in accordance with Method for Evaluating Detergency for Synthetic Kitchen Detergent in JIS K-3362, Testing Method of Synthetic Detergent. The test detergent was prepared by mixing polyoxyethylene alkylether sulfate, nonylcyclohexanol ethylene oxide adduct prepared in Reference Example 2, ethanol and water in a weight ratio of 16:3:6:75. Washing water was prepared by dissolving 1.5 g of the test detergent in 1 liter of water. As a result, the test detergent containing nonylcyclohexanol ethylene oxide adduct had excellent detergency as compared with an index detergent.

Test Example 4

Fiber Scouring Test

A scouring agent was prepared by mixing nonylcyclohexanol ethylene oxide adduct prepared in Reference Example 2, 40% aqueous solution of n-octylalcohol sulfate ester sodium salt, palm oil fatty acid and water in a ratio of 10:14:5. A scouring bath was prepared by dissolving 2 g of the scouring agent in 1 liter of water. A green ware of wool serge was immersed in the scouring bath in a bath ratio of 1:20. Scouring was carried out in a stainless steel beaker at 80° C. for 20 minutes. After scouring, rinse was carried out twice with warm water at 40° C. for 2 minutes each and flowing rinse was carried out with water for 2 minutes. Thereafter the wool serge was dehydrated, dried and extracted with diethyl ether for 4 hours in a Soxhlet extractor. The ratio of remaining lipid was measured on the resulting specimen. The ratio of remaining lipid was 0.11%, which illustrated good scouring ability.

Test Example 5

Deinking Test

Waste paper consisting of 70% by weight of waste newspaper elapsed two or three months after printing and 30% by weight of folded leaflet was shredded. To a bench disaggregation apparatus, 100 g of the shredded matter, 3 liter of water, 0.3% by weight of sodium hydroxide for waste paper, and 0.1% by weight of nonylcyclohexanol ethylene oxide adduct obtained in Reference Example 3 for waste paper as a deinking agent were charged and disaggregated for 10 minutes. The above was a disaggregation step.

The disaggregated sample was dehydrated with a Buchner funnel and concentrated to a waste paper concentration of 25 to 30%. Thereafter, 0.2% by weight for the waste paper of the same deinking agent as in the desaggregation step, 0.7% by weight for the waste paper of sodium hydroxide, 2.0% by weight for the waste paper of sodium silicate, and 0.7% by weight for the waste paper of hydrogen peroxide were added, thoroughly mixed and kneaded with a twin screw laboratory kneader at 300 rpm. The resulting sample was placed in a polyethylene bag and aged at 60° C. for 2 hours in a water bath. After aging, the sample was diluted to a waste concentration of 1% by addition of water, disaggregated for 10 minutes with the bench disaggregator, poured into a floatator to carry out floatation for 10 minutes. After floatation, the slurry of pulp was concentrated to 4% by 50 mesh wire, diluted to 1% concentration by addition of water, and a pulp sheet was prepared with a TAPPI standard sheet machine.

Measurement of Brightness

By using a photoelectric reflectance meter, blue reflectance of the pulp sheet obtained was measured at 457 µm.

Measurement of Residual Ink)

By using a microscope having a magnification of 200 times, numbers of ink residual in one visual field (0.1 cm$^2$) of the pulp sheet were measured. Measurement was carried out at different 10 points and measured values were averaged.

Measurement of Froth Amount

Amount of froth removed in floatation was measured as a guide for formability and yield. Increase in the froth amount indicates reduction of pulp yield.

The deinked pulp obtained in the test had a small amount (602 g) of froth, high brightness (57.6%) and small numbers of residual ink (12 particles)

Test Example 6

Yarn-making Ability Test

Fiber lubricating oil was prepared by mixing 45 parts by weight of lauryl laurate, 10 parts by weight of mineral oil, 35 parts by weight of nonylcyclohexanol ethylene oxide adduct prepared by Reference Example 3, 2 parts by weight of aliphatic diethanol-amide, 4 parts by weight of polyoxyethylenelaurylphosphate amine having an average ethylene oxide addition mole number of 3 and 4 parts by weight of sodium alkanesulfonate. Yarn making ability was evaluated by the following methods.
(1) Filament prepared: polyester filament, 75 denier, 36 filaments.
(2) Yarn making condition: spinning velocity 1500 mpm, wind up velocity 4500 mpm.
(3) Oil charge: An aqueous emulsion wherein the lubrication oil composition has a concentration of 15% by weight was prepared and charged on the roller. The oiling roller had a rotation velocity of 15 rpm.
(4) Evaluation: By using the above aqueous emulsion, filaments were spun with a spin-draw type spinning machine and numbers of fluff outside the pirn were counted.

Fluff numbers were 8, which illustrated good yarn-making ability.

Test Example 7

Test as an Emulsifier for Agricultural Chemicals

To a homomixer, 6 parts by weight of nonylcyclohexanol ethylene oxide adduct obtained in Reference Example 2, 36 parts by weight of fenthion, and 21 parts by weight of water were charged and stirred at 10,000 rpm for 10 minutes.

The agricultural chemicals were dispersed and an emulsified composition of agricultural chemicals formulation was obtained. Storage stability of the composition was examined by allowing to stand in a constant temperature chamber at 20° C. for 30 days. As a result, no separation was found at all and a good emulsified state was maintained.

Test Example 8

Test as an Emulsifier of Agricultural Chemicals

To a homomixer, 9 parts by weight of nonylcyclohexanol ethylene oxide adduct obtained in Reference Example 2, 36 parts by weight of chloropyriphosmethyl, 6 parts by weight of propylene glycol and 53 parts by weight of water were charged and stirred at 10,000 rpm for 10 minutes to obtain and emulsion of agricultural chemicals formulation.

Storage stability was examined by allowing to stand in a constant temperature chamber at 20° C. for 30 days. After the test, no separation was found at all and a good emulsified state was maintained.

Test Example 9

Test for an Emulsifier of Emulsion Polymerization

To a 500 ml flask equipped with a thermometer, stirrer, gas inlet tube, reflux condenser, and three dropping funnels, 120 g of water and 2 g of emulsifier nonylcyclohexanol ethylene oxide adduct obtained in Reference Example 4 were charged and heated to 60° C. under nitrogen ventilation. Thereafter, while maintaining the same temperature, 16 g of an unsaturated monomer mixture composed of butyl acrylate and styrene in a weight ratio of 1/1, 1.0 g of an aqueous solution containing 5% by weight of sodium persulfate, and 1.0 g of an aqueous solution containing 2.5% by weight of sodium hydrogen sulfate were dropwise added individually from each funnel at the same time to initiate polymerization. Thereafter, 64 g of the unsaturated monomer mixture was further added dropwise over 2 hours and simultaneously 5.7 g of an aqueous solution containing 5% by weight of sodium persulfate and 5.7 g of an aqueous solution containing 2.5% by weight of sodium hydrogen sulfate were dropwise added over 3 hours. After the dropwise addition, the reaction mass was maintained at the same temperature for 2 hours to complete the reaction. A high polymer emulsion was thus obtained.

Stability in the Polymerization Stage

The obtained high polymer emulsion was filtered through an 80 mesh metal net. The resulting solid portion was washed with water and dried. The weight of the dried solid was measured. As a result, 0.38% by weight of solid portion was formed for the unsaturated monomer charged.

Chemical Stability

The high polymer emulsion thus obtained was diluted with water to a concentration of 1% by weight and dropwise incorporated with a 0.5 mole/l aqueous calcium chloride solution. Concentration of calcium chloride in the emulsion was measured at the initiation time of coagulating emulsion particles. The concentration was 42 mmoles/l.

Test Example 10

Test for Dyeing Auxiliaries

Into a bath containing 0.25 g /l of a dyestuff represented by the following formula:

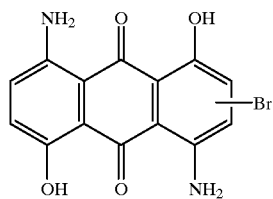

1 g/l of dinaphthylmethanedisulfonate and 0.2 g/l of dyeing auxiliaries nonylcyclohexanol ethylene oxide adduct obtained in Reference Example 2, a cloth of polyethyleneglycol terephthalate fiber was introduced at 60° C. in a bath-ratio of 1:40. Successively the bath was heated to 125° C. over 30 minutes and maintained the temperature for 60 minutes. The colored material thus obtained was uniformly dyed without unevenness and had high fixing ability.

Test Example 11

Test for Dyeing Auxiliaries

Into a bath containing 0.25 g/l of a dyestuff represented by the following formula:

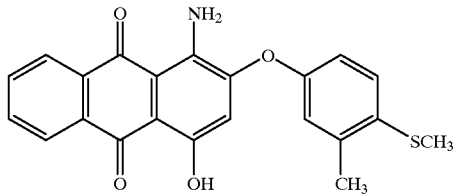

and 0.2 g/l of dyeing auxiliaries nonylcyclohexanol ethylene oxide adduct obtained in Reference Example 2, a cloth of polyethyleneglycol terephthalate fiber was introduced at 60° C. in a bath ratio of 1:40. The bath was heated to 125° C. over 30 minutes and maintained at the temperature for 60 minutes. The colored material thus obtained was uniformly dyed without unevenness and had high fixing ability.

Test Example 12

Test for an Antistatic Agent

A mixture was prepared from 100 g of polyvinyl chloride powder, 45 g of DOP, 2 g of a cadmium barium base stabilizer and 2 g of nonylcyclohexanol ethylene oxide adduct obtained in Reference example 2. The mixture thus obtained was kneaded with a baby roll at 180° C. for 1 minutes and formed into a film. The film was allowed to stand in a constant temperature and humidity room at 20° C., 60% RH, for 48 hours. After the test, the film had surface resistivity of $1.6 \times 10^{11}$ Ω.

As a comparative test, the same procedures were carried out without using nonylcyclohexanol ethylene oxide adduct obtained in Reference Example 2. The film thus obtained had surface resistivity $2.5 \times 10^{16}$ Ω.

Test Example 13

Test for an Antifogging Agent

A mixture was prepared from 100 parts by weight of polyvinyl chloride resin, 30 parts by weight of dioctyl phthalate, 10 parts by weight of dioctyl adipate, 5 parts by weight of tricresyl phosphate, 4 parts by weight of epoxy resin, 3 parts by weight of calcium-zinc based liquid stabilizer, 2 parts by weight of calcium-zinc base powder stabilizer and 2.5 parts by weight of antifogging agent nonylcyclohexanol ethylene oxide adduct obtained in Reference Example 2. The mixture thus obtained was kneaded on a hot roll at 180° C. to obtain a film having a thickness of 0.1 mm. The film was mounted on a head inclined box and allowed to stand for 12 hours at the outside air temperature of 5° C. at water temperature of 15° C. with an inclined angle of 10 degrees. Thereafter the wet state of the film was observed. Overall film surface was uniformly moistened into a transparent state. Further, the film was applied to an outdoor house and the wet state of the film was observed after 5 hours. Overall film surface was uniformly moistened into a transparent state.

Effect of the Invention

According to the process of the present invention, alkylcyclohexanol alkylene oxide adduct having 200 ppm or less content of alkylphenol and alkylphenol alkylene oxide adduct. Alkylcyclohexanol alkylene oxide adduct obtained by the process of the invention has less ultraviolet absorption and fluorescence due to alkylphenol alkylene oxide adduct, and thus the adduct is useful for spectrochemical analysis of protein and further has excellent properties also in the uses such as detergents and other common surfactant applications.

What is claimed is:

1. A process for preparing a high purity alkylcyclohexanol alkylene oxide adduct which has a narrow addition distribution of alkylene oxide and is represented by the formula (1):

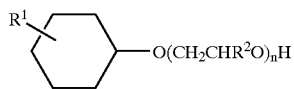
(1)

wherein $R^1$ is an alkyl group having 6 to 20 carbon atoms, $R^2$ is a hydrogen atom, methyl or ethyl group, and n is an integer of 1 or more, comprising the step of:

1) a hydrogenation step for reacting alkylphenol represented by the formula (4):

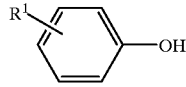
(4)

wherein $R^1$ is an alkyl group having 6 to 20 carbon atoms, with hydrogen in the presence of a hydrogenation catalyst to obtain a formed product consisting essentially of alkylcyclohexanol represented by the formula (3):

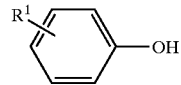
(3)

wherein $R^1$ is the same as above, 2) a first distillation step for distillating the formed product obtained in the hydrogenation step to give a fraction primarily consisting of alkylcyclohexanol and having an alkylphenol content 10 ppm by weight or less, 3) an alkylene oxide addition step for reacting one mole of alkylcyclohexanol obtained in the first distillation step with 1 to 5 moles of alkylene oxide having 2 to 4 carbon atoms in the presence of an acid catalyst to give alkylcyclohexanol alkylene oxide adduct, and 4) a second distillation step for separating unreacted alkylcyclohexanol and low boiling-point by-product of the reaction from alkylcyclohexanol alkylene oxide adduct obtained in the alkylene oxide addition step.

* * * * *

UNITED STATES PATENT AND TRADEMARK OFFICE
CERTIFICATE OF CORRECTION

PATENT NO. : 6,437,194 B2  Page 1 of 1
DATED : August 20, 2002
INVENTOR(S) : Yoshihisa Inoue et al.

It is certified that error appears in the above-identified patent and that said Letters Patent is hereby corrected as shown below:

<u>Title page,</u>
Item [75], Inventors, please delete "Daisuke Fukuoka, Yoshio Motoyama, and Kenji Shimamoto".

<u>Column 41,</u>
Line 22, please delete "STEP", and insert therefor -- STEPS --.

<u>Column 42,</u>
Line 17, please delete "PRIMARILY CONSISTING", and insert therefor
-- CONSISTING ESSENTIALLY --.

Signed and Sealed this

Tenth Day of February, 2004

JON W. DUDAS
*Acting Director of the United States Patent and Trademark Office*